(12) United States Patent
Kamata et al.

(10) Patent No.: US 12,102,437 B2
(45) Date of Patent: Oct. 1, 2024

(54) DATA ACQUISITION DEVICE AND BIOSENSOR

(71) Applicants: Nitto Denko Corporation, Ibaraki (JP); SPChange, LLC., Yokohama (JP)

(72) Inventors: Takatsugu Kamata, Yokohama (JP); Yusaku Hirai, Yokohama (JP); Masayuki Ueda, Yokohama (JP); Ryoma Yoshioka, Ibaraki (JP)

(73) Assignees: NITTO DENKO CORPORATION, Ibaraki (JP); SPCHANGE, LLC., Yokohama (JP)

( * ) Notice: Subject to any disclaimer, the term of this patent is extended or adjusted under 35 U.S.C. 154(b) by 476 days.

(21) Appl. No.: 17/442,952

(22) PCT Filed: Mar. 17, 2020

(86) PCT No.: PCT/JP2020/011737
§ 371 (c)(1),
(2) Date: Sep. 24, 2021

(87) PCT Pub. No.: WO2020/196099
PCT Pub. Date: Oct. 1, 2020

(65) Prior Publication Data
US 2022/0183604 A1    Jun. 16, 2022

(30) Foreign Application Priority Data

Mar. 27, 2019   (JP) .................................. 2019-060999
Mar. 27, 2019   (JP) .................................. 2019-061000

(51) Int. Cl.
*A61B 5/304*   (2021.01)
*A61B 5/00*    (2006.01)
(Continued)

(52) U.S. Cl.
CPC .............. *A61B 5/304* (2021.01); *A61B 5/257* (2021.01); *A61B 5/28* (2021.01); *A61B 5/308* (2021.01);
(Continued)

(58) Field of Classification Search
CPC .. A61B 2560/0209; A61B 5/308; A61B 5/304
See application file for complete search history.

(56) References Cited

U.S. PATENT DOCUMENTS 8,384,512 B2    2/2013  Onoshima et al.
9,735,893 B1 *  8/2017  Aleksov ............... A61B 5/0024
(Continued)

FOREIGN PATENT DOCUMENTS

CA    3 061 595 A1    10/2019
CN    101925943 A     12/2010
(Continued)

OTHER PUBLICATIONS

The Extended European Search Report issued on Apr. 19, 2022 for corresponding European Patent Application No. 20776320.2.
(Continued)

*Primary Examiner* — George R Evanisko
(74) *Attorney, Agent, or Firm* — Hauptman Ham, LLP

(57) ABSTRACT

A data acquisition device includes an integrated circuit and an information processor. The integrated circuit has a first terminal for receiving a master/slave switching signal upon start of data acquisition, an ADC for converting analog input data to digital data, and an output terminal for outputting the digital data. The information processor generates the master/slave switching signal, and has a second terminal connected to the first terminal and for outputting the master/slave switching signal, and an input terminal connected to the output terminal and for receiving the digital data. The information processor operates in the master mode when the
(Continued)

integrated circuit operates in the slave mode. The information processor operates in the slave when the integrated circuit operates in the master mode. The integrated circuit outputs the digital data when operating in the master mode according to the master/slave switching signal.

12 Claims, 9 Drawing Sheets

(51) Int. Cl.
*A61B 5/257* (2021.01)
*A61B 5/28* (2021.01)
*A61B 5/308* (2021.01)
*A61B 5/318* (2021.01)
*G06F 13/42* (2006.01)

(52) U.S. Cl.
CPC ............ *A61B 5/318* (2021.01); *A61B 5/6833* (2013.01); *A61B 2560/0209* (2013.01); *G06F 13/4282* (2013.01)

(56) References Cited

U.S. PATENT DOCUMENTS

| | | | |
|---|---|---|---|
| 2003/0224160 A1 | 12/2003 | Murakami et al. | |
| 2005/0137821 A1 | 6/2005 | Maher et al. | |
| 2008/0033259 A1 | 2/2008 | Manto et al. | |
| 2009/0096571 A1 | 4/2009 | Onoshima et al. | |
| 2010/0295832 A1 | 11/2010 | Nishio et al. | |
| 2014/0077985 A1 | 3/2014 | Tokunaga | |
| 2016/0172882 A1 | 6/2016 | Hatanaka et al. | |
| 2018/0027077 A1* | 1/2018 | Melodia | G16H 40/67 370/254 |
| 2018/0287625 A1 | 10/2018 | Murashima | |
| 2020/0093439 A1 | 3/2020 | Yoshioka | |
| 2022/0183604 A1 | 6/2022 | Kamata et al. | |

FOREIGN PATENT DOCUMENTS

| | | |
|---|---|---|
| CN | 103518328 A | 1/2014 |
| CN | 105393427 A | 3/2016 |
| CN | 108663584 A | 10/2018 |
| EP | 0495302 A2 | 7/1992 |
| JP | S64-8949 A | 1/1989 |
| JP | H2-99033 A | 4/1990 |
| JP | H4-341237 A | 11/1992 |
| JP | H6-167362 A | 6/1994 |
| JP | 2002-258999 | 9/2002 |
| JP | 2003-342541 A | 12/2003 |
| JP | 2004-83425 A | 3/2004 |
| JP | 2005-181337 A | 7/2005 |
| JP | 2007-5415 A | 1/2007 |
| JP | 2007-34959 A | 2/2007 |
| JP | 2007-58831 A | 3/2007 |
| JP | 2007-109185 | * 4/2007 |
| JP | 2007-109185 A | 4/2007 |
| JP | 2012-10978 A | 1/2012 |
| JP | 2015-210756 A | 11/2015 |
| JP | 2016-92648 A | 5/2016 |
| JP | 2016-166436 A | 9/2016 |
| JP | 2018-161324 A | 10/2018 |
| JP | 2018-186958 A | 11/2018 |
| WO | 2020/196099 A1 | 10/2020 |

OTHER PUBLICATIONS

Office Action issued on Nov. 17, 2022 for corresponding Canadian Patent Application No. 3,134,693 (3 pages).
International Search Report issued for corresponding International Patent Application No. PCT/JP2020/011737 on Jun. 23, 2020, along with an English translation.
Written Opinion issued for corresponding International Patent Application No. PCT/JP2020/011737 on Jun. 23, 2020.
The explanation of circumstances concerning accelerated examination submitted in corresponding Japanese Patent Application No. 2019-061000 on Oct. 1, 2019, along with an English translation.
The explanation of circumstances concerning accelerated examination submitted in corresponding Japanese Patent Application No. 2020-045993 on May 20, 2020 along with an English translation.
Office Action issued for corresponding Japanese Patent Application No. 2020-045993 on Jun. 16, 2020 along with an English machine translation.
Office Action issued for corresponding Japanese Patent Application No. 2020-045993 on Oct. 6, 2020 along with an English machine translation.
Official Action issued on Nov. 29, 2022, for corresponding European Patent Application No. 20 776 320.2 (5 pages).
Office Action issued on May 26 for corresponding European patent application No. 20776320.2 (6 pages).
Office Action issued on Mar. 7, 2022 for corresponding Indian Patent Application No. 202117043135, 6 pages.
Office Action issued on Jun. 7, 2022, for corresponding Australian Patent Application No. 2020246226.
Office Action issued on Dec. 6, 2023 for corresponding Canadian Patent Application No. 3,134,693 (4 pages).
Office Action issued on Mar. 16, 2024 for corresponding Chinese Patent Application No. 202080022920.7, along with an English machine translation (13 pages).

* cited by examiner

DATA ACQUISITION DEVICE AND BIOSENSOR

CROSS REFERENCE TO RELATED APPLICATION

This application is a National Stage of International Application No. PCT/JP2020/011737, filed on Mar. 17, 2020, which designates the United States and was published in Japan, and which is based upon and claims priority to Japanese Patent Application Nos. 1) 2019-060999, filed on Mar. 27, 2019; and 2) 2019-061000, filed on Mar. 27, 2019 in the Japan Patent Office. All of the aforementioned applications are hereby incorporated by reference in their entireties.

TECHNICAL FIELD

The present invention relates to a data acquisition device and a biosensor.

BACKGROUND ART

Conventionally, there has been a biosensor using a biocompatible polymer substrate which includes a plate-like first polymer layer, a plate-like second polymer layer, electrodes, and a data acquisition module (see, for example, Patent Document 1).

PRIOR ART DOCUMENT(S)

Patent Document(s)

Patent Document 1: JP 2012-010978 A

SUMMARY OF THE INVENTION

Technical Problem to be Solved

If such a data acquisition module or a biosensor is powered by a battery, reduction of power consumption is an issue.

Therefore, it is an objective of the present invention to provide a data acquisition device and a biosensor with reduced power consumption.

Technical Solution(s)

In the first aspect of the invention, a data acquisition device includes an integrated circuit and an information processor. The integrated circuit has a first terminal to which a master/slave switching signal is input at a start of data acquisition, an A/D converter for converting analog input data to digital data, and an output terminal for outputting the digital data. The integrated circuit operates either in a master mode or a slave mode according to the master/slave switching signal. The information processor has a switching setting part that generates the master/slave switching signal, a second terminal connected to the first terminal and for outputting the switching signal, and an input terminal connected to the output terminal and for receiving the digital data. The switching setting part configures the information processor to operate in the master when the integrated circuit operates in the slave, and configured the information processor to operate in the slave when the integrated circuit operates in the master mode. The integrated circuit outputs the digital data from the output terminal when the integrated circuit operates in the master mode according to the master/slave switching signal supplied from the information processor.

In the second aspect of the invention, a biosensor includes an electrode configured to be brought into contact with a subject, a data acquisition device configured to acquire analog electrocardiographic data acquired via the electrode, and a wiring that connects the electrode and the data acquisition device. The data acquisition device includes an integrated circuit and an information processor. The integrated circuit has a first terminal to which a master/slave switching signal is input at a start of acquisition of electrocardiographic data from the subject, an A/D converter for converting input analog electrocardiographic data to digital electrocardiographic data, and an output terminal for outputting the digital electrocardiographic data. The integrated circuit operates either in a master mode or a slave mode according to the master/slave switching signal. The information processor has a switching setting part that generates the master/slave switching signal, a second terminal connected to the first terminal and configured to output the switching signal, and an input terminal connected to the output terminal and configured to input the digital electrocardiographic data. The switching setting part configures the information processor to operate in the master mode when the integrated circuit operates in the slave mode, and to operate in the slave mode when the integrated circuit operates in the master mode. The integrated circuit outputs the digital electrocardiographic data from the output terminal when the integrated circuit operates in the master mode according to the master/slave switching signal supplied from the information processor.

Advantageous Effect of the Invention

A data acquisition device and a biosensor with reduced power consumption can be achieved.

DESCRIPTION OF PREFERRED EMBODIMENTS

Embodiments of a data acquisition device and a biosensor to which the data acquisition device is applied will be described below.

<Data Acquisition Device>

Figure 1:
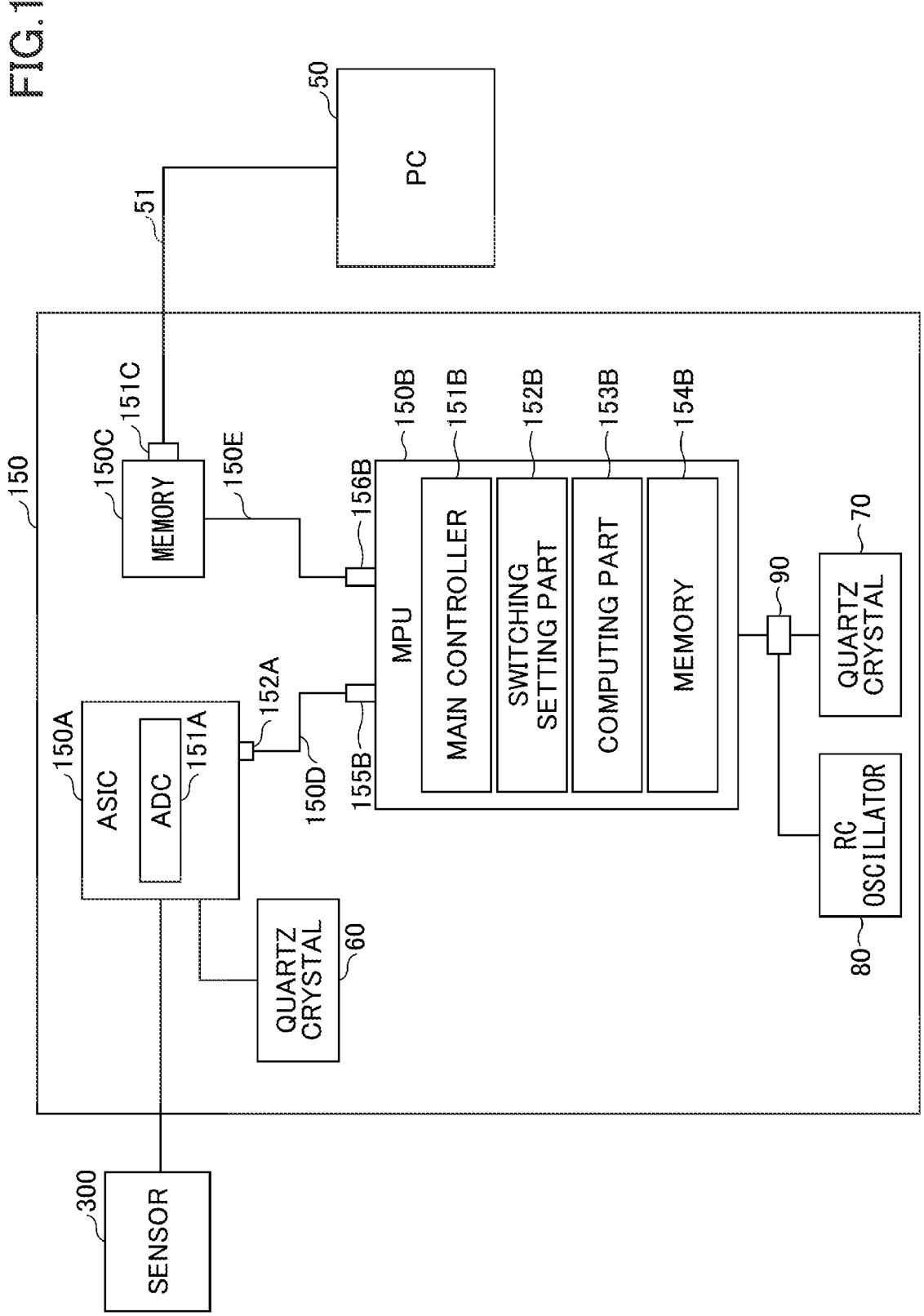
FIG. 1 is a schematic diagram of a data acquisition device.

FIG. 1 is a schematic diagram of a data acquisition device 150 according to an embodiment. The data acquisition device 150 is connected to a terminal or an electrode of an arbitrary device such as a sensor 300, to acquire target data. The sensor 300 may be one that detects, for example, biological signals representing electrocardiographic waveforms, brain waves, pulses, etc., but is not limited to this example. Although the embodiment will be described below based upon the sensor 300 configured to detect biological signals representing electrocardiographic waveforms (analog electrocardiographic data), the sensor 300 may be configured to detect a signal other than a biological signal, such as temperature, light, pressure, or geomagnetism.

The data acquisition device 150 includes an application specific integrated circuit (ASIC) 150A, a micro processing unit (MPU) 150B, a memory 150C, buses 150D and 150E, crystal quartz oscillators 60 and 70, an RC oscillator 80, and a switch 90. The buses 150D and 150E are, for example, serial peripheral interface (SPI) buses.

The ASIC 150A is connected to the sensor 300, and also connected to the MPU 150B via the bus 150D inside the data acquisition device 150. A crystal quartz oscillator 60 is connected to the ASIC 150A.

The ASIC 150A has an analog to digital converter (ADC) 151A and a terminal 152A. Components other than the ADC 151A and the terminal 152A of the ASIC 150A will be described later with reference to FIG. 2.

The ASIC 150A has a terminal compatible with the SPI interface. The ASIC 150A may operate in either a master mode or a slave mode with respect to the MPU 150B. Hereinafter, when operating in the master mode, the device may be referred to as a master, and when operating in the slave mode, the device may be referred to as a slave. Switching between operations in master mode and slave mode (master/slave switching) is performed by the MPU 150B. The device operating in the master mode controls operations of a plurality of devices involved in cooperative operations. The device operating in the slave mode operates according to a command or a control signal supplied from the master when the cooperative operations are performed by the plurality of devices. During the period of the data acquisition device 150 acquiring data from the sensor 300, the ASIC 150A is set to the master, while the MPU 150B is set to the slave, to suppress the power consumption.

The ADC 151A is, for example, a successive approximation register (SAR)/stochastic flash (SF) ADC, and an ADC described in, for example, JP 2016-092648 A can be used.

The ADC 151A converts the analog electrocardiographic data acquired by the sensor 300 into digital electrocardiographic data, and outputs the digital data to the MPU 150B.

The terminal 152A is connected to the MPU 150B via the bus 150D. Actually, the terminal 152A includes a plurality of terminals, including an M/S terminal for outputting a master/slave switching signal (hereinafter, referred to as a "switching signal), a slave select (SS) terminal, a mater-in slave-out (MISO) terminal, a master-out slave-in (MOSI) terminal, and clock (CLK) terminal.

The M/S terminal in the terminal 152A is an example of the first terminal to which the switching signal for switching between operations in the master mode and the slave mode is input from the MPU 150B. The MOSI terminal in the terminals 152A is an example of an output terminal, through which the ASIC 150A outputs digital electrocardiographic data to the MPU 150B when the ASIC 150A is set to the master and the MPU 150B is set to the slave.

The ASIC 150A divides the 32 MHz clock oscillated by the crystal quartz oscillator 60, and generates a 4 MHz system clock for internal use. This configuration will be described in more detail later with reference to FIG. 2.

The MPU 150B is an example of an information processor, and is connected to the ASIC 150A via the bus 150D, and connected to the memory 150C via the bus 150E. The RC oscillator 80 and the quartz crystal 70 are connected to the MPU 150B via a switch 90. The switch 90 is configured to selectively connects either one of the quartz crystal 70 and the RC oscillator 80 to the MPU 150B, and thus, the MPU 150B switches between the master and the slave.

The RC oscillator 80 outputs a clock having a frequency lower than the clock frequency of the quartz crystal 70. Although the clock frequency and the accuracy of the RC oscillator 80 are lower than those of the quartz crystal 70, power consumption of the RC oscillator 80 is less than that of a crystal oscillator using the quartz crystal 70.

The quartz crystal 70 and the RC oscillator 80 can be turned on and off by the MPU 150B. When the quartz crystal 70 is turned on, the RC oscillator 80 is turned off. When the RC oscillator 80 is turned on, the quartz crystal 70 is turned off.

The MPU 150B has a main controller 151B, a switching setting part 152B, a computing part 153B, a memory 154B, and terminals 155B and 156B. The main controller 151B, the switching setting part 152B, and the computing part 153B represent functional blocks of a computer realized by the MPU 150B. The memory 154B may be a memory built in the computer realized by the MPU 150B.

The main controller 151B is a processing part that controls the operations of the MPU 150B, and performs the operations other than those executed by the switching setting part 152B and the computing part 153B.

The switching setting part 152B configures the MPU 150B to operate as either the master or the slave. The switching setting part 152B generates a switching signal for switching the operations of the ASIC 150A between the master mode and the slave mode, and supplies the switching signal to the ASIC 150A.

The computing part 153B calculates a sum of the digital electrocardiographic data supplied from the ASIC 150A, and calculates the average of the summed-up data. For example, the computing part 153B performs addition every time digital electrocardiographic data item is acquired from the ASIC 150A, and calculates the average value every time the summation of eight digital electrocardiographic data items is obtained. Upon calculation of the average value, the computing part 153B saves the average value in the memory 150C.

The memory 154B stores programs and data required for the main controller 151B, the switching setting part 152B, and the computing part 153B of the MPU 150B to perform the respective operation. Further, the memory 154B may store the values calculated by the computing part 153B through the adding and averaging operation.

The terminal 155B includes a plurality of terminals such as an M/S terminal for outputting the switching signal, an SS terminal, a MISO terminal, a MOSI terminal, a CLK terminal, etc. The M/S terminal is an example of the second terminal configured to output the switching signal. The MOSI terminal is connected to the terminal 152A of the ASIC 150A. The MOSI terminal is an example of the input terminal through which digital electrocardiography data are input from the ASIC 150A when the ASIC 150A is the master and when the MPU150B is the slave.

The terminal 156B is connected to a personal computer (PC) 50 via the memory 150C and the cable 51, and outputs electrocardiographic data to the memory 150C when the MPU 150B is a slave.

The MPU 150B generates a system clock for internal use, based on the clock oscillated by the quartz crystal 70 or the RC oscillator 80. More specifically, the main controller 151B causes the quartz crystal 70 to oscillate. The main controller 151B and the quartz crystal 70 may compose a crystal oscillator.

The main controller 151B sets the system clock frequency high (32 MHz, for example) When the MPU 150B is the master, in order to set the operating frequency high. The main controller 151B sets the system clock frequency low (4 MHz, for example) When the MPU 150B is the slave, in order to reduce the operating frequency.

For the switching of the system clock frequency, the main controller 151B switches on and off of the quartz crystal 70 and the RC oscillator 80. The clock frequency generated by the quartz crystal 70 is 32 MHz, for example, and the clock frequency of the RC oscillator 80 is 16 MHz, for example. The main controller 151B generates the system clock of the MPU 150B based on the clock generated by either the quartz crystal 70 or the RC oscillator 80 by controlling the switch 90.

When the MPU 150B is the master, the main controller 151B uses the 32 MHz clock generated by the quartz crystal 70 as it is for the system clock, and also divides the 32 MHz clock of the quartz crystal 70 to generates a 4 MHz clock, in addition to the 32 MHz system clock. In serving as the master, the MPU 150B outputs the 4 MHz clock to the ASIC 150A, together with the switching signal, at a timing of outputting the switching signal to the ASIC 150A. The 4 MHz clock is output to the ASIC 150A from the CLK terminal of the terminals 155B.

When the MPU 150B is a slave, the main controller 151B divides the clock of the RC oscillator 80 to generate a 4 MHz system clock, and corrects the timing of the system clock using the chip select (CS) signal supplied from the ASIC 150A as a trigger. In this manner, the main controller 151B synchronizes the 4 MHz system clock obtained by dividing the clock of the RC oscillator 80 with the CS signal during the period when the MPU 150B is the slave. In addition, when the MPU 150B outputs the switching signal to the ASIC 150A, while serving as the slave, the MPU 150B outputs the 4 MHz system clock to the ASIC 150A together with the switching signal at the timing of outputting the switching signal. The 4 MHz clock is output to the ASIC 150A from the CLK terminal of the terminals 155B.

The reason why the 4 MHz system clock is generated based on the clock of the RC oscillator 80, when the MPU 150B is a slave, is to reduce the power consumption of the MPU 150B by reducing the system clock frequency. The quartz crystal 70 is used when the MPU 150B is the master, and is not used when the MPU 150B is the slave.

The memory 150C is connected to the MPU 150B via the bus 150E. The memory 150C is, for example, a NAND flash memory, and has a capacity required for storing target data. If the sensor 300 is a stick-on biosensor, it has a capacity of storing a required amount of electrocardiographic data acquired from the stick-on biosensor. For example, the stick-on biosensor is attached to the chest of a living body for about 24 hours to acquire analog electrocardiographic data. In this case, the memory 150C has a capacity of storing the electrocardiographic data detected for at least 24 hours. The MPU 150B may perform arithmetic averaging on the digital electrocardiographic data input from the ASIC 150A, and then save the calculated data in the memory 150C.

The memory 150C has a terminal 151C. A cable 51 connected to the PC 50 can be connected to the terminal 151C. The electrocardiographic data saved in the memory 150C can be transferred to the PC 50 via the cable 51.

Figure 2:
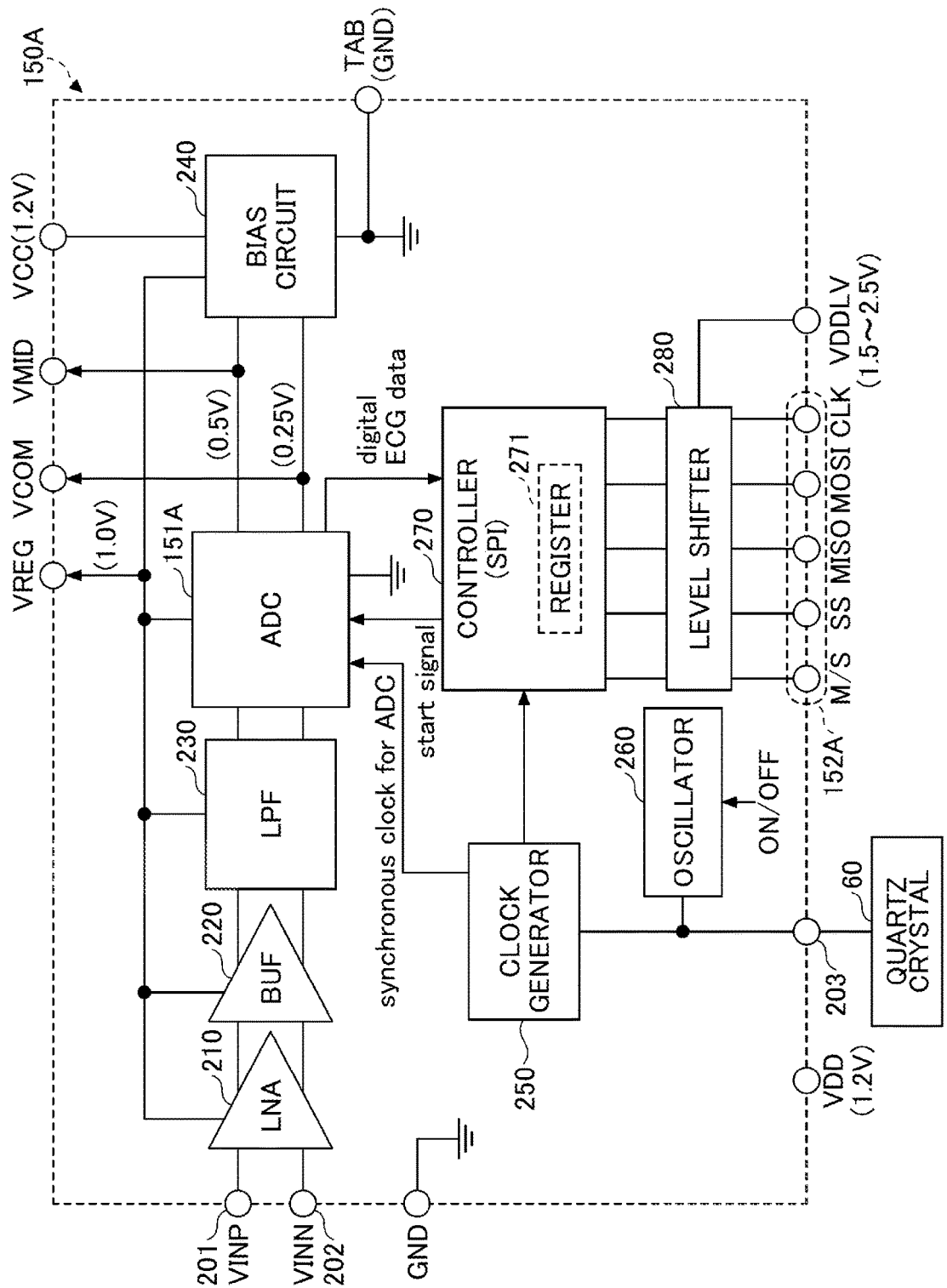
FIG. 2 is a diagram showing the configuration of ASIC 150A.

FIG. 2 shows the configuration of the ASIC 150A. The ASIC 150A includes an input terminal (VINP) 201, an input terminal (VINN) 202, a CLK terminal 203, a terminal 152A, an low noise amplifier (LNA) 210, a buffer (BUF) 220, a low pass filter (LPF) 230, an ADC 151A, a bias circuit 240, a clock generator 250, an oscillator 260, a controller 270, and a level shifter 280.

In addition to these components, the ASIC 150A has a VREG terminal, a VCOM terminal, a VMID terminal, a VCS terminal, a TAB terminal (at the GND potential level), a GND terminal, a VDD terminal (1.2V), a VDDLV terminal (1.5V to 2.5V), etc.

The input terminals 201 and 202 are connected to the sensor 300. A positive (plus) signal is input to the input terminal 201, and a negative (minus) signal is input to the input terminal 201.

The CLK terminal 203 is connected to a quartz crystal 60 which is provided outside the ASIC 150A.

The terminal 152A is connected to the MPU150B, as has been described above with reference to FIG. 1, and it includes the M/S terminal, the SS terminal, the MISO terminal, the MOSI terminal, and the CLK terminal.

The LNA 210 is connected between the input terminals 201 and 202 and the BUF 220, and amplifies the analog electrocardiographic data input from the input terminals 201 and 202. The amplified analog data is output from the LNA 210.

The BUF 220 is connected between the LNA 210 and the ADC 151A to shape the waveform of the analog electrocardiographic data amplified by the LNA 210 and output the shaped data to the LPF 230.

The LPF 230 is connected between the BUF 220 and the ADC 151A, and configured to allow only a predetermined low frequency band of the analog electrocardiographic data input from the BUF 220 to pass through to remove noise.

The ADC 151A operates based on the clock signal input from the clock generator 250. The ADC 151A converts the analog electrocardiographic data input from the LPF 230 into digital electrocardiographic data, and outputs the digital electrocardiographic data to the controller 270. The clock signal input from the clock generator 250 determines the sampling cycle of the ADC 151A, and is a 4 MHz clock signal, for example. The frequency of the clock signal supplied from the clock generator 250 is set lower than that of the system clock (32 MHz, for example) used in the MPU 150B when the MPU 150B is the master.

The bias circuit 240 converts the power supply voltage (1.2V) input to the VCS terminal into a voltage required by the ADC 151A (0.5V and 0.25V, for example), and outputs the converted voltage. The bias circuit 240 is, for example, a voltage divider circuit.

The clock generator 250 includes a phase locked loop (PLL) and a frequency divider, and is configured to generate a clock having a predetermined frequency (4 MHz, for example) from the clocks supplied from the quartz crystal 60 and the oscillator 260, and to output the generated clock to the ADC 151A and the controller 270. The clock generator 250 divides the 32 MHz clock generated by the quartz crystal 60 to generate a 4 MHz system clock internally used by the ASIC 150A. The clock generator 250 also outputs the 4 MHz system clock to the ADC 151A, the controller 270, and other components.

The oscillator 260 is an integrated circuit (IC) which causes the quartz crystal 60 to oscillate. The oscillator 260 and the quartz crystal 60 compose a crystal oscillator. The oscillator 260 and the quartz crystal 60 oscillate at a clock of 32 MHz, for example.

The controller 270 is realized by a combinational circuit, and has a register 271. The controller 270 receives and outputs data between the ADC 151A and the level shifter 280. The controller 270 operates according to the command input from the terminal 152A via the level shifter 280. For example, the controller 270 switches the ASIC 150A between the master and the slave based on the switching signal input from the M/S terminal via the level shifter 280.

Upon switching the ASIC 150A to the master based on the switching signal from the MPU 150B, the controller 270 outputs a start signal to ADC 151 to cause the ADC 151 to start analog to digital (AD) conversion, and outputs a CS signal to the MPU 150B. When the ASIC 150A has been switched to the master, the controller 270 causes the clock generator 250 to output a synchronous clock for AD conversion, and outputs the synchronous clock for AD conversion to the MPU 150B. The start signal, the CS signal, and the synchronous clock for AD conversion are synchronized with the system clock of the ASIC 150A. In this example, the synchronous clock for AD conversion and the system clock are both 4 MHz clocks, which are the same clocks.

The start signal is output once from the register 271 to the ADC 151A when the ADC 151A starts AD conversion. More specifically, to cause the ADC 151A to perform the AD conversion, an H-level pulse is output from the register 271 to the ADC 151A only once.

The CS signal is output from the controller 270 to the MPU 150B, via the level shifter 280 and the SS terminal of the terminal 152A. The CS signal is a signal output by the control unit 270 to the MPU 150B. The CS signal is a synchronizing signal to allow the MPU 150B to acquire digital electrocardiographic data.

The synchronous clock for AD conversion is used by the ADC 151A when AD conversion is performed, and is output from the clock generator 250 to the ADC 151A. The ADC 151A performs AD conversion when the synchronous clock rises to the H level.

The ADC 151A performs AD conversion, synchronized with the synchronous clock for AD conversion output from the clock generator 250, and the MPU 150B takes the digital electrocardiographic data in at the timing when the CS signal changes from the high (H) level to the low (L) level. Thus, the digital conversion process in the ADC 151A and the data acquisition at the MPU 150B can be synchronized. The frequency of the CS signal is, for example, 2 to 8 times higher than the system clock frequency of the ASIC 150A.

The controller 270 supplies the digital electrocardiographic data output from the ADC 151A to the level shifter 280 when the ASIC 150A is the master. The digital electrocardiographic data is output from the level shifter 280 to the MPU 150B via the MOSI terminal. The controller 270 outputs and receives other commands and data to and from the MPU 150B via the level shifter 280 and the terminal 152A.

The register 271 holds the digital electrocardiographic data output from the ADC 151A, and the start signal and the CS signal output by the control unit 270 to the ADC 151A. The register 271 may serve as a data holding unit.

The level shifter 280 adjusts the signal level of data, commands, etc. between the control unit 270 and the terminal 152A.

Figure 3:
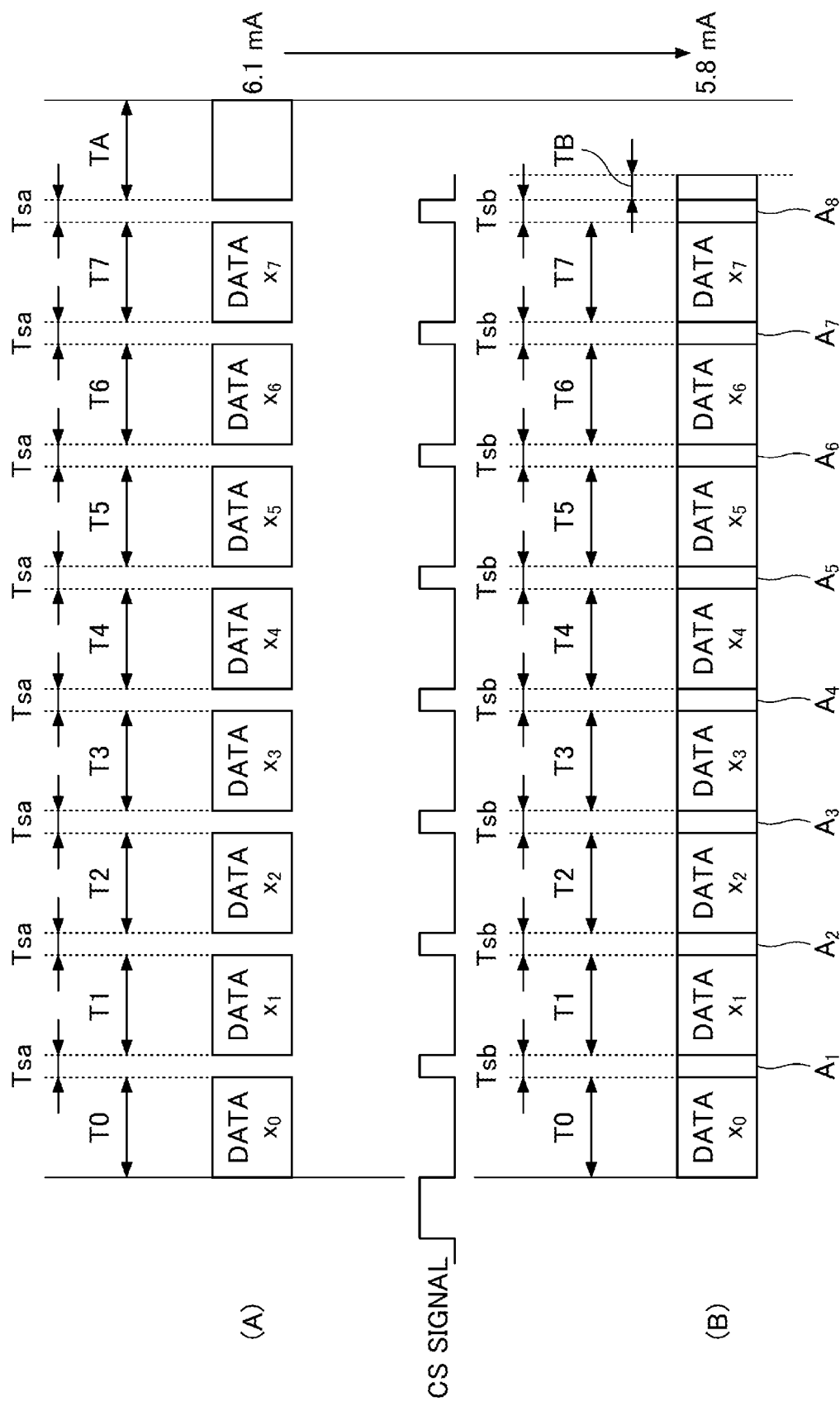
FIG. 3 is a timing chart of operations of the MPU 150B.

FIG. 3 is a timing chart showing the operations of the MPU 150B. FIG. 3 (A) shows the timing of a comparative example in which the MPU performs the adding process and the averaging process after data items x0 to x7 have been acquired. FIG. 3 (B) shows the process timing of the embodiment in which addition is performed every time the MPU 150B acquires one of the data items x0 to x7, and averaging is performed every eight data items.

Data items x0 to x7 are digital electrocardiographic data, and the horizontal axes in FIGS. 3 (A) and (B) represent time.

As shown in FIG. 3 (A), the MPU of the comparative example sequentially acquires data items x0 to x7 according to the system clock. The time durations of section T0 to T7 required acquire the respective data items x0 to x7 are equal to each other. The time section Tsa inserted between adjacent ones of the section T0 to T7 is used to transfer the acquired data to the memory. In the MPU of the comparative example, after the first data item x0 to the eighth data item x7 are acquired and transferred to the memory, the data items x0 to x7 are read out from the memory in the time section TA to calculate the summation A of the data items x0 to x7 according to formula (1), and calculate the average value A/8 based on the summation A.

$$A = \sum_{n=0}^{7} x_n \quad (1)$$

After the average value A/8 is determined using the summation A, the comparative process of the MPU starts to acquire data item x0 in the next cycle, and repeats the process of FIG. 3 (A).

In contrast, in the embodiment shown in FIG. 3 (B), the MPU 150B acquires each of the data items x0 to x7 from the ASIC 150A every time the CS signal transitions from the H level to the L level at the beginning of each of the time sections T0 to T7. Every time one of the data items x0 to x7 is acquired, addition is performed in the time section Tsb according to formula (2).

$$A_{n+1} = A_n + x_n \quad (2)$$

where $A_0 = 0$, and $n = 0, 1, 2, \ldots, 7$.

In the adding process, every time one of the data items x0 to x7 is acquired, the acquired data value is added to the previously calculated sum $A_n$.

The sums A1 to A8 are determined in the eight time sections Tsb, respectively, immediately after the corresponding time sections T0 to T7 for acquiring data items x0 to x7. The sum A8 represents the summation of the data items x0 to x7. The starting point of time section TB is the beginning of the time section T0 of the next cycle. Accordingly, the MPU 150B acquires data item x0 from the ASIC 150A upon the transition of the CS signal from the H level to the L level at the beginning of the time section T0.

Upon acquisition of the eighth data item x7 and calculation of the sum A8, the MPU 150B calculates the average value A8/8 using the sum A8 in the next time section TB.

In this manner, the MPU 150B of the embodiment performs the addition according to the formula (2) in each of the eight time sections Tsb upon acquiring one of the data item x0 to x7. Both the time section Tsb in FIG. 3 (B) and the time section Tsa in FIG. 3 (A) are time intervals inserted between tasks so as to allow the MPU 150B to perform interrupt processing in the background, and accordingly, the time section Tsb in FIG. 3 (B) and the time section Tsa in FIG. 3 (A) are substantially the same.

In the time section TB following the time section T7 for calculating the sum A8, only the average value A8/8 is calculated based on the sum A8. The time section TB can be significantly shortened, compared with the time section TA in FIG. 3 (A).

Power consumptions of the MPU of the comparative example and the MPU of the embodiment were simulated, assuming that the MPUs of the comparative example and the embodiment are applied to stick-on biosensors to perform the respective processes of FIG. 3 (A) and FIG. 3 (B). It was confirmed from the simulation result that the power consumption was reduced from 6.1 mA to 5.8 mA by the process of FIG. 3 (B).

This simulation result is equivalent to enhancement of the continuous use time of a battery increased from 33 hours to 40 hours under the condition that the same battery 160 is used in the stick-on biosensors using the MPU of the comparative example and the MPU of the embodiment. Because the stick-on biosensor using the MPU of the embodiment consumes less power than the stick-on biosensor using the MPU of the comparative example, the continuous usable time can be increased by about 20%.

Upon calculation of the average value A8/8 using the sum A8, the main controller 151B of the MPU 150B transfers the average value A8/8 to the memory 150C and saves it in the memory 150C. The arithmetic averaging is performed in order to reduce the noise level of the digital electrocardiographic data and to improve the S/N ratio.

Figure 4:
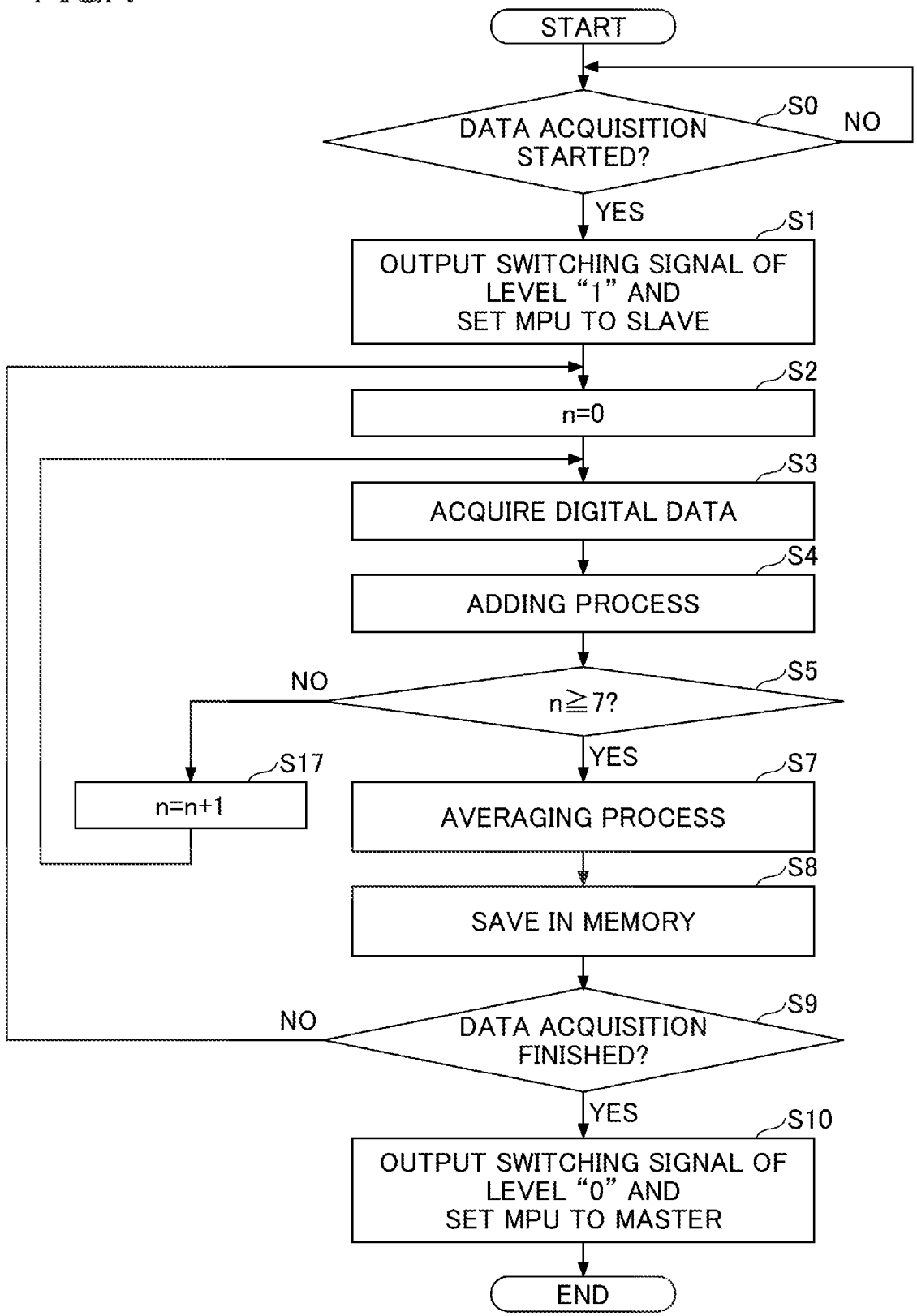
FIG. 4 is a flowchart showing a processing example of the MPU150B.

FIG. 4 is a flowchart showing the operations of the MPU 150B. The flowchart of FIG. 4 shows a process from the start to the end of the data acquisition from the sensor 300 and recording of the data, and this process is repeatedly performed by the MPU 150B during a predetermined period of time.

When the process starts, the MPU 150B determines whether the data acquisition has started (in step S0). This step may be implemented by determining whether the data acquisition device 150 has been connected to the sensor 300, whether the data has been transferred from the sensor 300 to the data acquisition device, whether a prescribed time has come, etc. Step S0 is repeated until it is determined that data acquisition has started (YES in S0). If data acquisition has started, the switching setting part 152B sets the switching signal level to "1" and outputs it to the ASIC 150A, while setting the MPU 150B to a slave (step S1). The ASIC 150A is set to the master by the switching signal having a level "1".

The computing part 153B initialize "n" to zero (n=0) (step S2).

The computing part 153B acquires digital data from the ASIC 150A according to the CS signal (step S3).

The computing part 153B performs an adding process according to the formula (2) (step S4).

The computing part 153B determines whether n is seven (7) or greater (step S5).

If it is determined by the computing part 153B that n is not equal to or greater than 7 (NO in S5), n is incremented (step S6).

If it is determined by the computing part 153B that n is 7 or greater (YES in S5), the computing part 153B calculates the average value (A8/8) based on the sum A8 (step S7).

The computing part 153B saves the average value (A8/8) in the memory 150C (step S8).

The main controller 151B determines whether the data acquisition is finished (step S9). This step may be implemented by determining whether the data acquisition device 150 has been disconnected from the sensor 300, whether the data transfer from the sensor 300 has not been carried out for a certain period of time or longer, whether the data occupancy of the memory 150C has exceeded a certain level, etc. If the sensor 300 is a stick-on biosensor, it may be determined that the data acquisition has been completed when twenty four (24) hours have passed from the start of recording the digital electrocardiographic data.

If it is determined by the main controller 151B that the data acquisition has not been completed (NO in S9), the operation flow returns to step S2 to repeat steps S2 to S9.

If it is determined by the main controller 151B that the data acquisition is finished (YES in S9), the switching setting part 152B sets the switching signal level to "0", and outputs the switching signal to the ASIC 150A, while setting the MPU 150B to the master (step S10). Upon being set to the slave by the switching signal of level "0", the ASIC 150A stops the ADC 151A from implementing the digital conversion process. Thus, the ASIC 150A causes the ADC 151A to perform digital conversion process during the period when the switching signal is at level "1", and causes the ADC 151A to terminate the digital conversion process when the switching signal transitions to level "0". In other words, the ADC 151A continues to perform the digital conversion process while the ASIC 150A is the master.

In the foregoing process, summation of the digital data items and averaging are performed over the data acquisition period, the calculation results are saved in the memory 150C.

In this manner, every time the data acquisition device 150 acquires one of the data items x0 to x7, the acquired data value is successively added to the previously calculated sum according to the formula (2) in the corresponding time section Tsb immediately after the data acquisition. In the time section TB immediately after the calculation of the eighth sum A8, only the average value (A8/8) is calculated based on the sum A8. Accordingly, the processing time for obtaining the arithmetic average can be shortened, and the power consumption can be reduced.

Thus, the data acquisition device 150 with reduced power consumption can be achieved.

The data acquisition device 150 sets the ASIC 150A to the master, while setting the MPU 150B to the slave, during the period when the MPU 150B calculates the sum $A_{n+1}$ and the average value (A8/8) using the sum A8 as shown in FIG. 3 (B). In this state, the system clock frequency of the MPU 150B is reduced to 4 MHz, which is equal to the sampling frequency of the ADC 151A. This configuration also contributes to the reduction of the power consumption.

The MPU 150B acquires digital electrocardiographic data from the ASIC 150A in response to the change of the CS signal to the L level, while the MPU 150 itself is set to the slave. The MPU 150B can acquire the digital electrocardiographic data, without requesting the ASIC 150A to transmit the digital electrocardiographic data to the MPU 150B. The MPU 150B can immediately take in the digital electrocardiographic data acquired by the controller 270 from the ADC 151A, and is capable of real-time performance. Thus, the data acquisition device 150 with successful real-time performance can be achieved.

Although, in the foregoing example, eight data items are added in one cycle by the MPU 150B to calculate an arithmetic average, the number of data items is not limited to the above-described example, and any number of data items may be added for the calculation of the arithmetic average as long as two or more data items are added.

In the foregoing, the internally used system clock is produced by the MPU 150B, when the MPU 150B is the master, based on the clock generated by the quartz crystal 70. However, the MPU 150B may produce the internally used system clock based on the clock generated by the quartz crystal 60 connected to the ASIC 150A, while the MPU 150B is the master. In this case, the MPU 150B may be configured to receive the clock of the quartz crystal 60 from the ASIC 150A. With this configuration, the data acquisition device 150 does not have to be furnished with the quartz crystal 70 and the switch 90. Further, the main controller 151B may produce a system clock based on the clock oscillated by the quartz crystal 60 when the MPU 150B is the master, and produce a system clock based on the clock of the RC oscillator 80 when the MPU 150B is the slave.

<Application to Biosensor>

An example configuration in which the data acquisition device 150 is applied to a biosensor 100 is described.

Figure 5:
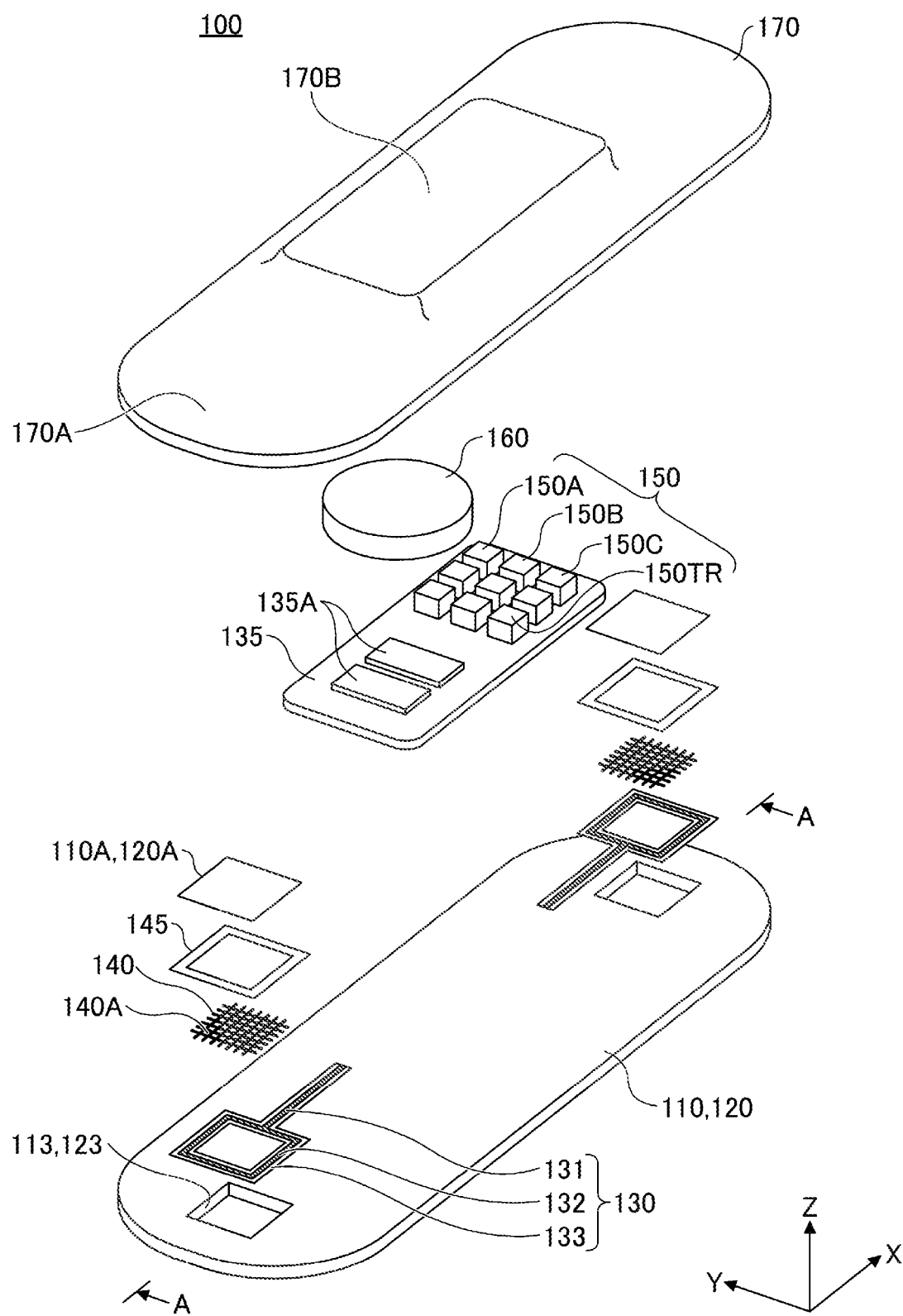
FIG. 5 is an exploded view of a biosensor of the embodiment.
Figure 6:
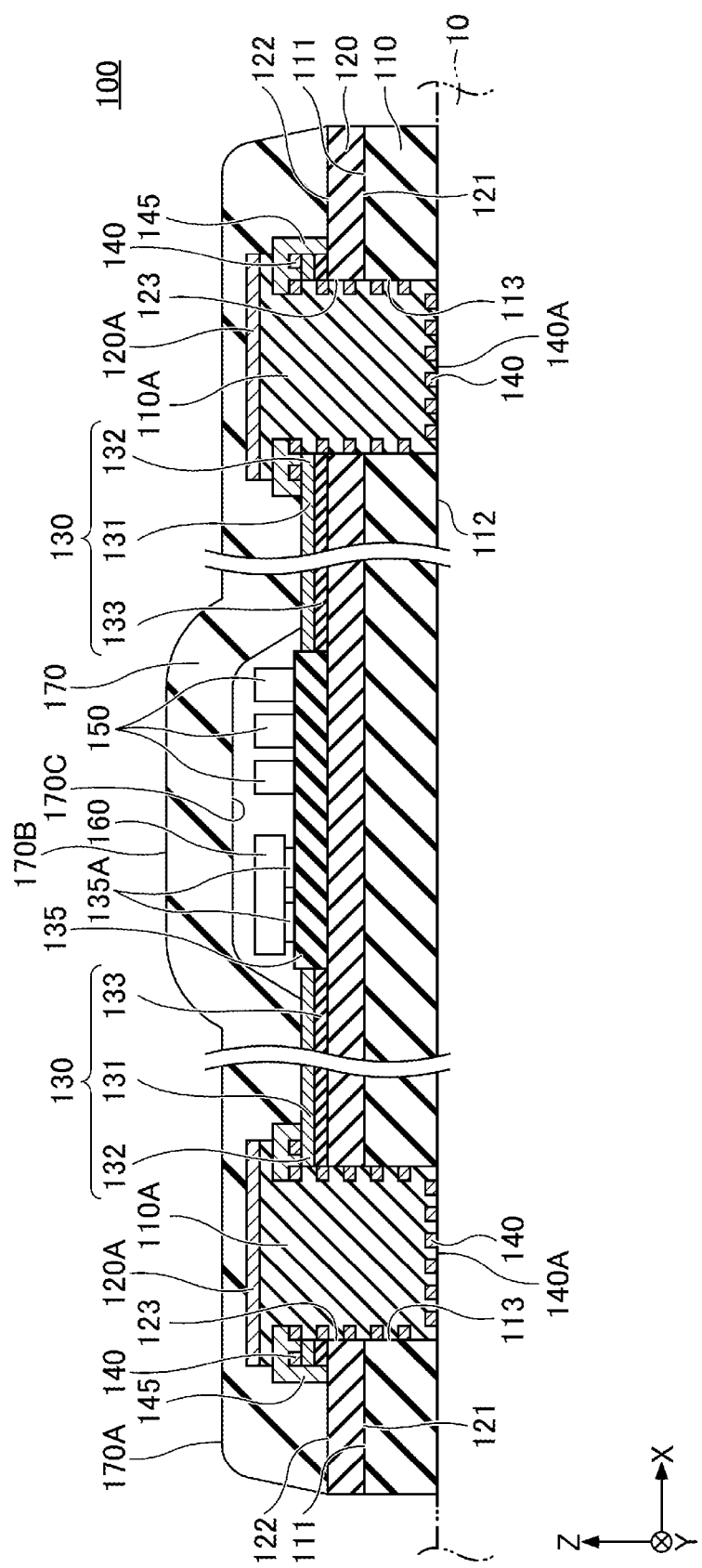
FIG. 6 is a cross-sectional view of the assembled biosensor, which corresponds to the cross section taken along the A-A line in FIG. 5.

FIG. 5 is an exploded view of the biosensor 100 according to an embodiment. FIG. 6 is a cross-sectional view of the assembled biosensor 100, taken along the A-A line of FIG. 5. The biosensor 100 includes, as the main components, a pressure-sensitive adhesive layer 110, a base material layer 120, a circuit unit 130, a substrate 135, a probe 140, a fixing tape 145, the data acquisition device 150, a battery 160, and a cover 170.

In the following, the XYZ coordinate system is defined. For convenience of explanation, the −Z direction opposite to the stacking direction is referred to as the lower side or the bottom side, and the +Z direction parallel to the stacking direction is referred to as the upper side or the top side; however, such directional terms do not intend to represent the absolute directional relationship.

The embodiment is described exemplifying the biosensor 100 which is brought into contact with a living body or a subject to detect biological information. The living body may be a human body or a non-human creature, and the biosensor 100 is attached to the skin, scalp, forehead, etc. of the living body. Each of the components composing the biosensor 100 will be described below.

The electrode which comes into contact with the living body (or the subject) is called a probe 140, and a fixing tape 145 is used as an example of the bonding means. A pair of electrodes are provided as the probes 140 in order to measure biological information in a single channel. Single channel measurement is to acquire one biometric information through a pair of (or two) electrodes.

The biosensor 100 is a sheet-like sensor having an elongated elliptical shape in a plan view. The bottom surface (the lower-most surface in the −Z direction) of the biosensor 100 is an adhering surface to be attached to the skin 10 of the living body. The upper surface (the surface opposite to the adhering surface) of the biosensor 100 is covered with the cover 170.

The circuit unit 130 and the substrate 135 are mounted on the upper surface of the base material layer 120. The probes 140 are embedded in the pressure-sensitive adhesive layer 110 so as to be exposed at the lower surface 112 of the pressure-sensitive adhesive layer 110. The lower surface 112 (see FIG. 6) of the pressure-sensitive adhesive layer 110 is the adhering surface of the biosensor 100.

The pressure-sensitive adhesive layer 110 is a flat plate-like adhesive layer. The pressure-sensitive adhesive layer 110 has a longitudinal axis extending in the X direction, and a short axis in the Y direction. The pressure-sensitive adhesive layer 110 is supported by the base material layer 120, and is attached to the lower surface 121 of the base material layer 120 in the −Z direction.

As shown in FIG. 6, the pressure-sensitive adhesive layer 110 has an upper surface 111 and a lower surface 112. The upper surface 111 and the lower surface 112 are flat surfaces. The pressure-sensitive adhesive layer 110 is a layer for sticking the biosensor 100 to the living body. The lower surface 112 has pressure-sensitive adhesiveness, and can adhere to the skin 10 of the living body.

The pressure-sensitive adhesive layer 110 has through holes 113. The through holes 113 have the same size and shape as the through holes 123 formed in the base material layer 120, and are provided at the same positions as the through holes 123 in a plan view so as to be connected to each other.

The material of the pressure-sensitive adhesive layer 110 is not particularly limited as long as it has pressure-sensitive adhesiveness, and it may have biocompatibility. Examples of the material of the pressure-sensitive adhesive layer 110 include an acrylic pressure-sensitive adhesive and a silicone-based pressure-sensitive adhesive. Among these, an acrylic pressure-sensitive adhesive is preferably used.

Acrylic pressure-sensitive adhesive contains an acrylic polymer as the main component.

Acrylic polymer is contained as a pressure-sensitive adhesive component. One example of the acrylic polymer is a polymer produced by polymerizing a monomer component which contains (meth)acrylic acid ester such as isononyl acrylate or methoxyethyl acrylate as a main material, and contains a monomer capable of copolymerization with the (meth)acrylic acid ester as an optional material. The content of the main material in the monomer component is 70 mass % to 99 mass %, and the content of the optional material in the monomer component is 1 mass % to 30 mass %. As the acrylic polymer, (meth)acrylic acid ester-based polymer described in JP 2003-342541 A may be used.

The acrylic pressure-sensitive adhesive may further contain a carboxylic acid ester.

The carboxylic acid ester contained in the acrylic pressure-sensitive adhesive serves as a modifier for reducing the pressure-sensitive adhesiveness of the acrylic polymer to adjust the adhesive strength of the pressure-sensitive adhesive layer 110. The carboxylic acid ester is miscible or compatible with the acrylic polymer.

An example of the carboxylic acid ester is glyceryl tri-fatty acid ester.

The content of the carboxylic acid ester is preferably 30 to 100 parts by mass, and more preferably 50 to 70 parts by mass, with respect to 100 parts by mass of the acrylic polymer.

The acrylic pressure-sensitive adhesive may contain a cross-linking agent, as necessary. The cross-linking agent is a cross-linker for cross-linking the acrylic polymer. Examples of the cross-linking agent include, but are not limited to polyisocyanate compounds, epoxy compounds, melamine compounds, peroxide compounds, urea compounds, metal alkoxide compounds, metal chelate compounds, metal salt compounds, carbodiimide compounds, oxazoline compounds, aziridine compounds, and amine compounds. These cross-linking agents may be used alone or in combination. The cross-linking agent is preferably a polyisocyanate compound (polyfunctional isocyanate compound).

The content of the cross-linking agent is preferably, for example, 0.001 to 10 parts by mass, and more preferably 0.01 to 1 part by mass with respect to 100 parts by weight of the acrylic polymer.

Preferably, the pressure-sensitive adhesive layer 110 has satisfactory biocompatibility. For example, according to the keratin peeling test performed on the pressure-sensitive adhesive layer 110, the keratin peeled area ratio is preferably 0% to 50%, more preferably 1% to 15%. Within the range of 0% to 50% of the keratin peeled area ratio, the load on the skin 10 (see FIG. 2) can be suppressed when the pressure-sensitive adhesive layer 110 is attached to the skin 10. The keratin peeling test may be performed by the measuring method described in JP 2004-83425 A.

The moisture permeability of the pressure-sensitive adhesive layer 110 is 300 (g/m$^2$/day) or higher, preferably 600 (g/m$^2$/day) or higher, and more preferably 1000 (g/m$^2$/day) or higher. With the moisture permeability of the pressure-sensitive adhesive layer 110 of 300 (g/m$^2$/day) or higher, the load on the skin 10 (see FIG. 2) can be suppressed when the pressure-sensitive adhesive layer 110 is attached to the skin 10.

The pressure-sensitive adhesive layer 110 may be considered biocompatible when it satisfies at least one of the following conditions; the condition that the keratin peeled area ratio measured by the keratin peeling test is 50% or less, or the condition that the moisture permeability is 300 (g/m$^2$/day) or higher. It is more preferable for the material of the pressure-sensitive adhesive layer 110 to satisfy both conditions. In this case, the pressure-sensitive adhesive layer 110 is more biocompatible in a stable manner.

The thickness of the pressure-sensitive adhesive layer 110 between the upper surface 111 and the lower surface 112 is preferably 10 μm to 300 μm. With the thickness of the pressure-sensitive adhesive layer 110 of 10 μm to 300 μm, the stick-on biosensor 100 can be made thinner, and in particular, the stick-on biosensor 100 except for the data acquisition device 150 can be made thinner.

The base material layer 120 is a support layer configured to support the pressure-sensitive adhesive layer 110. The pressure-sensitive adhesive layer 110 is bonded to the lower surface 121 of the base material layer 120. The circuit unit 130 and the substrate 135 are provided on the upper surface side of the base material layer 120.

The base material layer 120 is a flat plate-like (or sheet-like) member made of an insulator. The shape of the base material layer 120 is the same as the shape of the pressure-sensitive adhesive layer 110 in a plan view, and they are aligned to and stacked with each other.

The base material layer 120 has a lower surface 121 and an upper surface 122, both of which are flat surfaces. The lower surface 121 is in contact with the upper surface 111 of the pressure-sensitive adhesive layer 110 by pressure-sensitive adhesion. The base material layer 120 may be made of a flexible resin having appropriate elasticity, flexibility and toughness. For example, a thermoplastic resin such as polyurethane resin, silicone resin, acrylic resin, polystyrene resin, vinyl chloride resin or polyester resin may be used. The thickness of the base material layer 120 is 1 to 300 μm, preferably 5 to 100 μm, and more preferably 10 to 50 μm.

The lower limit of the elongation at break of the base material layer 120 is preferably 100% or more, more preferably 200% or more, still more preferably 300% or more. With the elongation at break of 100% or more, the material of the base material layer 120 exhibits satisfactory elasticity. The upper limit of the elongation at break of the base material layer 120 may be appropriately designed according to the thickness of the base material layer 120 or the other factors, and it may be 2000% or less. The elongation at break can be measured with a test piece type 2 at a tensile speed of 5 mm/min according to JIS K 7127 (1999).

The lower limit of the tensile strength of the base material layer 120 at 20° C. (at chuck spacing of 100 mm, tensile speed of 300 mm/min, and strength at break) is preferably 0.1 N/20 mm or higher, more preferably 1 N/20 mm or higher. The upper limit of the tensile strength of the base material layer 120 at 20° C. can be appropriately designed according to the material and the thickness of the base material layer 120, and it may be 20 N/20 mm or less. The tensile strength can be measured based on the JIS K 7127 (1999) standard.

The upper limit of the tensile storage modulus E' of the base material layer 120 at 20° C. is preferably 2,000 MPa or less, more preferably 1,000 MPa or less, further preferably 100 MPa or less, even more preferably 50 MPa or less, and most preferably 20 MPa or less. If the upper limit of the tensile storage modulus E' of the base material layer 120 is 2,000 MPa or less, the base material layer 120 can have satisfactory elasticity. The lower limit of the tensile storage modulus E' can be appropriately designed according to the material and the thickness of the base material layer 120, and it may be 0.1 MPa or more. The tensile storage modulus E' of the base material layer 120 at 20° C. can be determined by measuring the dynamic viscoelasticity of the base material layer 120 under the conditions of frequency of 1 Hz and heating rate of 10° C./min.

If at least one of the requirements of the elongation at break of 100% or more, the tensile strength of 20 N/20 mm or less, and the tensile storage modulus E' of 2,000 MPa or less is satisfied, the base material layer 120 has elasticity. From the viewpoint of allowing the base material layer 120 to exhibit more elasticity, it is preferable that two or more of the above requirements are satisfied, and is more preferable that the three requirements are satisfied.

The peel strength of the base material layer 120 with respect to the copper foil is preferably 0.5 N/cm or higher, more preferably 1.0 N/cm or higher, further preferably 2.0 N/cm or higher, and most preferably 2.5 N/cm or higher. If the peel strength is at or above the lower limit, separation between the base material layer 120 and the wiring 131 can be reliably suppressed. The peel strength may be measured by preparing a sample with a 1 cm width, which is a lamination of the base material layer 20 and a copper foil, and by peeing the base material layer 120 from the copper foil using a tensile tester under the conditions of a peeling angle of 180 degrees and a peeling speed of 30 mm/min.

The thickness of the base material layer 120 is preferably 1 μm to 300 μm, more preferably 5 μm to 100 μm, and even more preferably 10 μm to 50 μm.

The base material layer 120 is formed of a base material composition. The base material composition contains a base resin as a main component.

The base resin is, for example, a flexible resin capable of imparting appropriate elasticity, flexibility, and toughness to the base material layer 120. Examples of the base resin include thermoplastic resins such as polyurethane-based resins, silicone-based resins, acrylic-based resins, polystyrene-based resins, vinyl chloride-based resins, and polyester-based resins. From the viewpoint of ensuring more satisfactory elasticity of the base material layer 120, it is preferable to use a polyurethane resin.

The circuit unit 130 may include wiring 131, a frame 132, and a substrate 133. The circuit unit 130 is connected to the electrode via the frame 132, and connected to the data acquisition device 150 via the wiring 131. The biosensor 100 has two circuit units 130. The wiring 131 and the frame 132 are integrally formed on the upper surface of the substrate 133. The wiring 131 connects the frame 132 to the data acquisition device 150 and the battery 160.

The wiring 131 and the frame 132 may be made of copper, nickel, gold, or alloys thereof. The thickness of the wiring 131 and the frame 132 is preferably 0.1 μm to 100 μm, more preferably 1 μm to 50 μm, and still more preferably 5 μm to 30 μm.

The two circuit units 130 are provided corresponding to two through holes 113 of the pressure-sensitive adhesive layer 110 and two through holes 123 of the base material layer 120. The wiring 131 is connected to the data acquisition device 150 and the terminal 135A of the battery 160 via the wiring on the substrate 135. The frame 132 is a conductive member shaped in a rectangular loop, which is larger than the through hole 123 of the base material layer 120.

The substrate 133 has the same shape as the wiring 131 and the frame 132 in a plan view. A part of the substrate 133, in which the frame 132 is provided, has a rectangular frame area larger than the opening of the through hole 123 of the base material layer 120. The frame 132 and the rectangular frame area of the substrate 133 in which the frame 132 is formed, are placed on the upper surface of the base material layer 120 so as to surround the through hole 123. The substrate 133 is made of an insulator, and a polyimide substrate or film may be used as the substrate 133. Because the base material layer 120 has adhesiveness (or tacking property), the substrate 133 is fixed to the upper surface of the base material layer 120.

The substrate 135 is an insulative substrate on which the data acquisition device 150 and the battery 160 are mounted, and is provided on the upper surface 122 of the base material layer 120. For the substrate 135, a polyimide substrate or film may be used. Wiring and the terminal 135A for the battery 160 are provided on the upper surface of the substrate 135. The wiring of the substrate 135 is connected to the data acquisition device 150 and the terminal 135A, and is also connected to the wiring 131 of the circuit unit 130.

The two probes 140 are a pair of electrodes which come into contact with a subject. Specifically, the pair of electrodes come into contact with skin 10 to detect a biological signal when the pressure-sensitive adhesive layer 110 is attached to the skin 10. The biological signal is an electric signal representing, for example, electrocardiographic waveforms, and detected as analog electrocardiographic data. The biological signal represents a potential difference between the electrical voltages sensed by the two probes 140.

The electrodes used as the probes 140 are fabricated using a conductive composition containing at least a conductive polymer and a binder resin, which will be described later. Further, each of the electrodes is fabricated by punching a sheet-like member formed of the conductive composition using a mold or the like, so as to be suitable for the probe.

The probe 140 has, for example, a rectangular shape in a plan view, and has holes 140A arranged in a matrix, which are larger than the through holes 113 of the pressure-sensitive adhesive layer 110 and the through holes 123 of the base material layer 120. Along the edges (i.e., the four sides) of the probe 140, ladder-like protrusions extending in the X direction and the Y direction may be formed. The electrode used as the probe 140 may have a predetermined pattern. Examples of the electrode pattern include a mesh pattern, a stripe pattern, or such a pattern that multiple electrodes are exposed at the sticking surface.

The fixing tape 145 is an example of the bonding part of the present embodiment. The fixing tape 145 is, for example, a copper tape shaped into a rectangular loop in a plan view. An adhesive is applied to the lower surface of the fixing tape 145. The fixing tape 145 is provided over the frame 132 along the four sides of the probe 140 so as to surround the openings of the through holes 113 and 123 in a plan view to fix the probe 140 to the frame 132. The fixing tape 145 may be a metal tape other than copper.

The fixing tape 145 may be a non-conductive tape such as a resin tape composed of a non-conductive resin base and an adhesive, in place of a metal tape such as a copper tape. However, a conductive or metal tape may be preferable because the probe 140 can then be electrically connected to the frame 132 of the circuit unit 130, while securing the probe 140 onto the frame 132.

The probe 140 is secured to the frame 132 such that the four sides overlap the frame 132, using the fixing tape 145, which is applied so as to cover the periphery of the probe 40. The fixing tape 145 adheres to the frame 132 through the holes 140A of the probe 140.

The pressure-sensitive adhesive layer 110A and the base material layer 120A are placed over the fixing tape 145 and the probe 140, while keeping the four sides of the probe 140 secured to the frame 132 by the fixing tape 145, and pressed downward into the through holes 113 and 123. The probe 140 is pushed into the through holes 113 and 123 along the inner walls thereof, and the pressure-sensitive adhesive layer 110A penetrates through the holes 140A of the probe 140.

The probe 140 is pushed downward until the center area of the probe 140 substantially aligns with the lower surface 112 of the pressure-sensitive adhesive layer 110, while keeping the four edges fixed to the frame 132 by the fixing tape 145. Accordingly, when the probe 140 is pressed against the skin 10 of a living body, the pressure-sensitive adhesive layer 110A adheres to the skin 10 to keep the probe 140 in tight contact with the skin 10.

The thickness of the probe 140 is preferably less than that of the pressure-sensitive adhesive layer 110. The thickness of the probe 140 is preferably 0.1 to 100 μm, more preferably 1 to 50 μm.

The peripheral area of the pressure-sensitive adhesive layer 110A, which forms a rectangular frame area surrounding the center area in the plan view, is located on the fixing tape 145. Although in FIG. 6, the upper surface of the pressure-sensitive adhesive layer 110A is substantially flat, the center area may be slightly indented lower than the peripheral area. In either case, the base material layer 120A may be superposed on the upper surface of the pressure sensitive adhesive layer 110A.

The pressure-sensitive adhesive layer 110A may be made of the same materials as the pressure-sensitive adhesive layer 110, and the base material layer 120A may be made of the same materials as the base material layer 120. Alternatively, the pressure-sensitive adhesive layer 110A may be made of a different material from the pressure-sensitive adhesive layer 110, or the base material layer 120A may be made of a different material from the base material layer 120.

Although in FIG. 6 the thicknesses of the respective parts are exaggerated for clarifying the structure, the thickness of the pressure-sensitive adhesive layers 110 and 110A is 10 μm to 300 μm, and the thickness of the base material layers 120 and 120A is 1 μm to 300 μm in the actual configuration. The thickness of the wiring 131 may be 0.1 μm to 100 μm, the thickness of the substrate 133 may be about several hundred microns, and the thickness of the fixing tape 145 may be 10 μm to 300 μm.

With the configuration of FIG. 6 in which the probe 140 and the frame 132 are in direct contact with each other to ensure electrical connection, the fixing tape 145 may be a non-conductive resin tape or the like.

In FIG. 6, the fixing tape 145 covers the edges of the frame 132 and the substrate 133, together with the sides of the probe 140, and it reaches the upper surface of the base material layer 120. However, the fixing tape 145 may not reach the upper surface of the base material layer 120, or may not cover the edges of the substrate 133 and the frame 132, because it is sufficient for the fixing tape 145 to be able to bond the probe 140 and the frame 132.

The substrate 133 and the two substrates 135 may be monolithically formed. In this case, wiring 131, two frames 132, and the terminal 135A are formed on the surface of the monolithic substrate, on which the data acquisition device 150 and the battery 160 are mounted.

The electrode used as the probe 140 may be fabricated by thermosetting and molding a conductive composition described below. The conductive composition contains a conductive polymer, a binder resin, and at least one of a cross-linking agent or a plasticizer.

As the conductive polymer, for example, polythiophene, polyacetylene, polypyrrole, polyaniline, polyphenylene vinylene, or the like can be used. These materials may be used either individually or in combinations of two or more polymers. It is preferable to use, among these, a polythiophene compound. From the viewpoint of lower contact impedance with the living body and higher conductivity, it is preferable to use PEDOT/PSS obtained by doping polystyrene sulfonic acid (poly 4-styrene sulfonate abbreviated as PSS) to poly 3,4-ethylenedioxythiophene (PEDOT).

The content of the conductive polymer is preferably 0.20 to 20 parts by mass with respect to 100 parts by mass of the conductive composition. With the above range of the conductive polymer, satisfactory conductivity, toughness, and flexibility can be imparted to the conductive composition. The content of the conductive polymer is more preferably 2.5 to 15 parts by mass, and further preferably 3.0 to 12 parts by mass with respect to the conductive composition.

As the binder resin, either a water-soluble polymer or a water-insoluble polymer can be used. From the viewpoint of compatibility with other components contained in the conductive composition, it is preferable to use a water-soluble polymer for the binder resin. The water-soluble polymer includes a hydrophilic polymer which may not be completely soluble in water, but has hydrophilicity.

For the water-soluble polymer, a hydroxyl group-containing polymer or the like can be used. The hydroxyl group-containing polymer includes saccharides such as agarose, polyvinyl alcohol (PVA), modified polyvinyl alcohol, and a copolymer of acrylic acid and sodium acrylate. These materials may be used individually or in combinations of two or more polymers. Among these, polyvinyl alcohol and modified polyvinyl alcohol are preferable, and modified polyvinyl alcohol is more preferable.

Examples of the modified polyvinyl alcohol include acetacetyl group-containing polyvinyl alcohol, and diacetone acrylamide modified polyvinyl alcohol. As the diacetone acrylamide-modified polyvinyl alcohol, a diacetone acrylamide-modified polyvinyl alcohol-based resin (DA-modified PVA-based resin) described in JP 2016-166436 A can be used, for example.

The content of the binder resin is preferably 5 to 140 parts by mass, with respect to 100 parts by mass of the conductive composition. With this content range of the binder resin, conductivity, toughness, and flexibility can be satisfactorily imparted to the conductive composition. The content of the binder resin is more preferably 10 to 100 parts by mass, and further preferably 20 to 70 parts by mass with respect to the conductive composition.

The cross-linking agent and the plasticizer have properties to impart toughness and flexibility to the conductive composition. By imparting flexibility to the molded product of the conductive composition, an elastic electrode can be obtained. Thus, the probe 140 having elasticity is fabricated.

Toughness is a property that achieves both strength and elongation (extensibility). Regarding the toughness, one of the strength and the elongation may be remarkably high, while the other is not remarkably low, such that the strength and the elongation are well balanced.

Flexibility is a property that can suppress damage or breakage even when the molded body (i.e., the electrode sheet) of the conductive composition is bent.

The cross-linking agent crosslinks the binder resin. By mixing the cross-linking agent in the binder resin, the toughness of the conductive composition can be enhanced. Preferably, the cross-linking agent has reactivity with a hydroxyl group. Using such a cross-linking agent, the cross-linking agent can react with the hydroxyl group contained in a binder resin formed of a hydroxyl group-containing polymer.

Examples of the cross-linking agent include zirconium compounds such as zirconium salts; titanium compounds such as titanium salts; borates such as boric acid; isocyanate compounds such as blocked isocyanate; aldehyde compounds such as dialdehyde (e.g., glyoxal); alkoxyl group-containing compounds, and methylol group-containing compounds. Any one or a combination of two or more of these may be used. From the viewpoint of reactivity and safety, a zirconium compound, an isocyanate compound, and an aldehyde compound are preferable.

The content of the cross-linking agent is preferably 0.2 to 80 parts by mass, with respect to 100 parts by mass of the conductive composition. With this content range of the cross-linking agent, satisfactory toughness and flexibility can be imparted to the conductive composition. The content of the cross-linking agent is more preferably 1 to 40 parts by mass, and more preferably 3.0 to 20 parts by mass.

The plasticizer improves the tensile elongation and flexibility of the conductive composition. Examples of the plasticizer include glycerin, ethylene glycol, propylene glycol, sorbitol, polyol compounds with these polymers, and aprotonic compounds such as N-methylpyrrolidone (NMP), dimethylformamide (DMF), NN'-dimethylacetamide (DMAc), or dimethyl sulfoxide (DMSO). Any one or a combination of two or more of these materials may be used. Among these, glycerin is preferable from the viewpoint of compatibility with other components.

The content of the plasticizer is preferably 0.2 to 150 parts by mass, with respect to 100 parts by mass of the conductive composition. With this content range of the plasticizer, satisfactory toughness and flexibility can be imparted to the conductive composition. The content of the plasticizer is more preferably 1.0 to 90 parts by mass, and further preferably 10 to 70 parts by mass with respect to 100 parts by mass of the conductive polymer.

Adding either the cross-linking agent or the plasticizer to the conductive composition is sufficient. By adding the cross-linking agent or the plasticizer in the conductive composition, the toughness and flexibility of the molded product of the conductive composition can be improved.

If the conductive composition contains a cross-linking agent, without containing a plasticizer, the toughness of the molded product of the conductive composition can be further improved. That is, the resultant product has improved tensile strength, tensile elongation, and flexibility.

If the conductive composition contains a plasticizer, without containing a cross-linking agent, the tensile elongation of the molded product of the conductive composition can be improved, and therefore, toughness is imparted to the molded product of the conductive composition as a whole. The flexibility of the molded product of the conductive composition can also be improved.

It may be preferable that both the cross-linking agent and the plasticizer are contained in the conductive composition. By adding both the cross-linking agent and the plasticizer to the conductive composition, the toughness of the molded product of the conductive composition may be further improved.

In addition to the above-described components, the conductive composition may contain a surfactant, a softener, a stabilizer, a leveling agent, an antioxidant, an anti-hydrolysis agent, a swelling agent, a thickener, a colorant, a filler, or other known additives, at an appropriate ratio. Examples of the surfactant include silicone-based surfactants.

The conductive composition is prepared by mixing the above-described components in the above-described ratios.

The conductive composition may contain a solvent in an appropriate ratio, as necessary. In this case, an aqueous solution of the conductive composition is appropriately prepared.

The solvent may be an organic solvent or an aqueous solvent. Examples of the organic solvent include ketones such as acetone or methyl ethyl ketone (MEK); esters such as ethyl acetate; ethers such as propylene glycol monomethyl ether; and amides such as N, N-dimethylformamide. Examples of the aqueous solvent include water; and alcohol for methanol, ethanol, propanol, isopropanol, etc. Among these, an aqueous solvent may be preferably used.

At least one of the conductive polymer, the binder resin, and the cross-linking agent may be used in a form of an aqueous solution dissolved in a solvent. In this case, the above-described aqueous solvent can be preferably used.

The data acquisition device 150 is provided on the upper surface 122 of the base material layer 120, and is electrically connected to the wiring 131. The data acquisition device 150 processes a biological signal acquired via the electrode used as the probe 140. The data acquisition device 150 has a rectangular shape in the cross-sectional view. Terminals are provided on the lower surface (−Z direction) of the data acquisition device 150. Examples of the material for the terminals of the data acquisition device 150 include solder, conductive paste, or the like.

As shown in FIG. 5, the data acquisition device 150 may include a wireless communication unit 150TR, in addition to the ASIC 150A, the MPU 150B, the memory 150C. The data acquisition device 150 is connected to the probes 140 and the battery 160 via the circuit units 130.

The ASIC 150A includes the ADC, as has been described above with reference to FIG. 1. The data acquisition device 150 is driven by the electric power supplied from the battery 160 and acquires the biological signal measured by the probes 140. The data acquisition device 150 performs data processing such as filtering or digital conversion on the acquired analog electrocardiographic data. The MPU 150B calculates the arithmetic average of multiple electrocardiographic data items which are acquired and digitalized over multiple time sections, and saves the data in the memory 150C. The data acquisition device 150 can continuously acquire analog electrocardiographic data for a certain period of time, e.g., 24 hours. Because the data acquisition device 150 may be used for continuous measurement of biological signals (such as analog electrocardiographic data) for a long duration, a configuration with reduced power consumption is advantageous, as has been described above with reference to FIG. 1 to FIG. 4.

The wireless communication unit 150TR is a transceiver used when the digital electrocardiographic data are read out from the memory 150C by a test equipment for evaluation test, via radio communication at a frequency of, for example, 2.4 GHz. The evaluation test is, for example, a JIS 60601-2-47 standard test. The evaluation test is performed after the completion of assembling the biosensor 100 to confirm the performance of the biosensor 100 which serves as a medical device for detecting biological signals. The evaluation test requires that the attenuation ratio of the signal output from the biosensor 100 with respect to the biological signal detected by the biosensor 100 is less than 5%. This evaluation test is performed on all of the final products.

A command such as an evaluation test start command, or a measurement start command may be input to the MPU 150B via the wireless communication unit 150TR using a function on the web browser of a smartphone or the PC in which the application program dedicated to the biosensor 100 is installed.

Although the embodiment is described based on the configuration of the data acquisition device 150 having the wireless communication unit 150TR, a connector for connecting the cable of the test equipment may be provided to the data acquisition device 150, in place of the wireless communication unit 150TR, so that the biological signals are read through the connector.

As shown in FIG. 6, the battery 160 is provided on the upper surface 122 of the base material layer 120. A lead-acid battery, a lithium ion secondary battery, or the like can be used as the battery 160. The battery 160 may be a button cell or a coin battery. The battery 160 has electrical terminals provided on its bottom surface. Two terminals of the battery 160 are connected to the probe 140 and the data acquisition device 150 via the circuit unit 130. The capacity of the battery 160 is determined so that the data acquisition device 150 can measure the biological signals (analog electrocardiographic data) for 24 hours or longer, for example.

The cover 170 covers the entirety of the base material layer 120, the circuit unit 130, the substrate 135, the probe 140, the fixing tape 145, the data acquisition device 150, and the battery 160. The cover 170 has a base 170A and a protrusion 170B protruding from the center of the base 170A in the +Z direction. The base 170A shapes a basic form of the cover 170 in a plan view, and extends in a plane lower than the protrusion 170B. A recess 170C is formed on the bottom side of the protrusion 170B. The bottom surface of the base 170A of the cover 170 is adhered to the upper surface 122 of the base material layer 120. The substrate 135, the data acquisition device 150, and the battery 160 are housed in the recess 170C. Thus, the cover 170 is provided to the upper surface 122 of the base material layer 120 with the data acquisition device 150 and the battery 160 accommodated in the recess 170C.

The cover 170 serves not only as a cover to protect the circuit unit 130, the data acquisition device 150, and the battery 160 provided on the base material layer 120, but also as a shock absorber to protect the internal components from possible impacts applied from the above to the stick-on biosensor 100. The cover 170 is formed of, for example, silicone rubber, soft resin, urethane, or the like.

Figure 7:
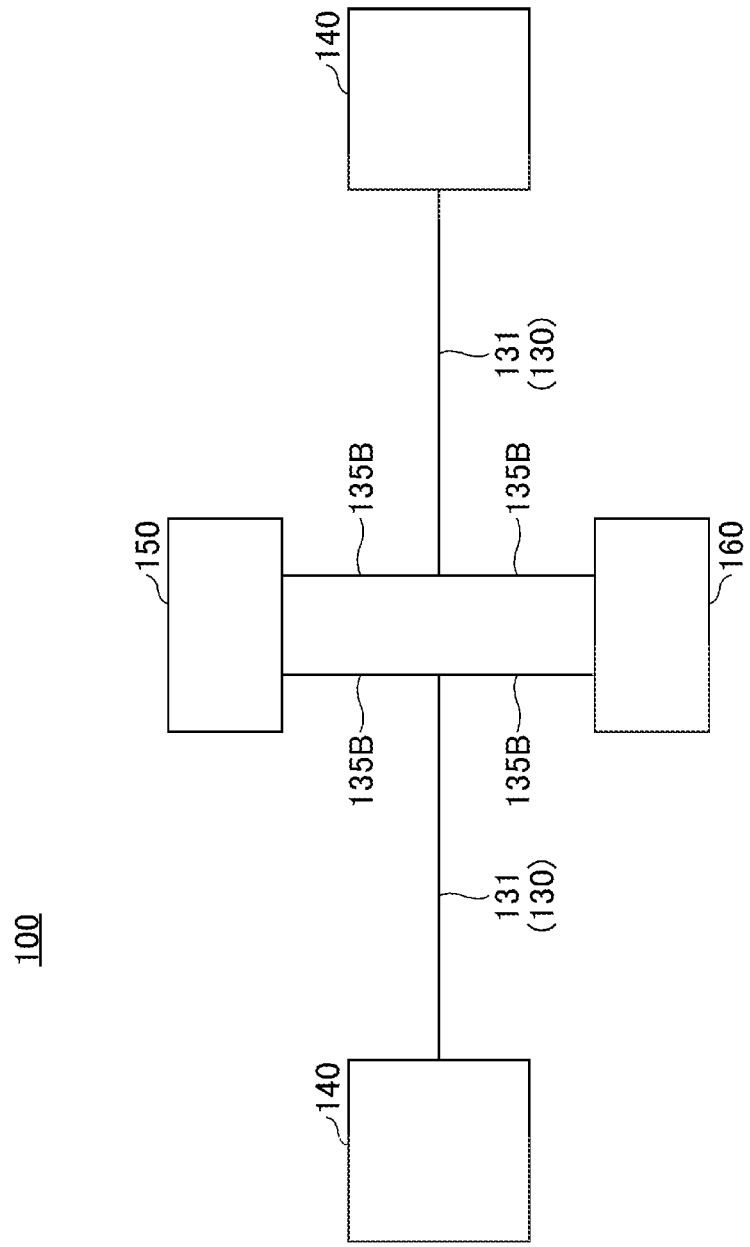
FIG. 7 shows the circuit configuration of the biosensor.

FIG. 7 is a diagram showing a circuit configuration of the biosensor 100. Each of the probes 140 is connected to the data acquisition device 150 and the battery 160 via the wiring 131 and the wiring 135B of the substrate 135. The two probes 140 are connected in parallel to the data acquisition device 150 and the battery 160.

Figure 8:
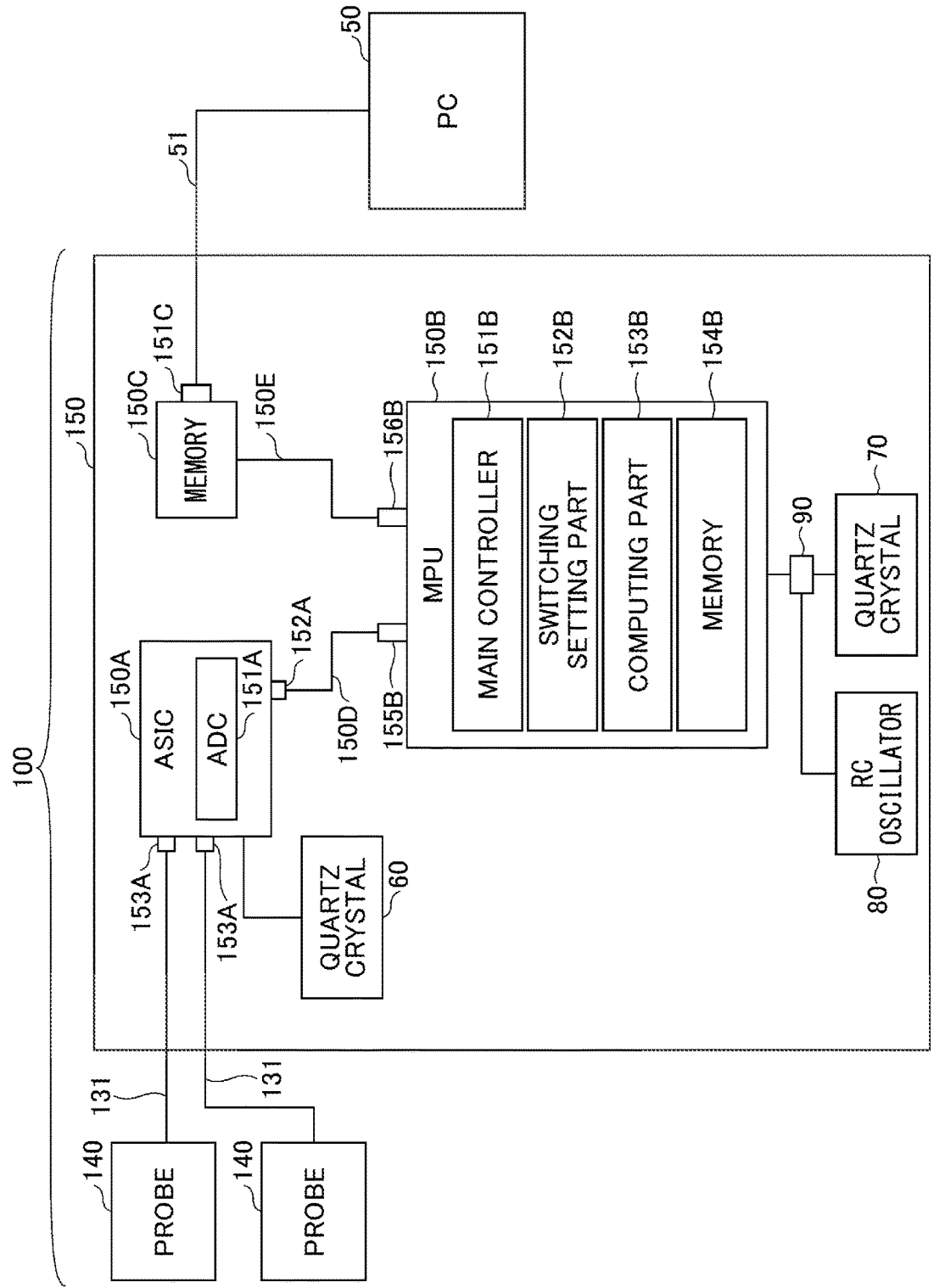
FIG. 8 is a schematic diagram of a data acquisition device applied to a biosensor.

FIG. 8 is a schematic diagram of the data acquisition device 150 applied to the biosensor 100. The detailed structure and operations of the data acquisition device 150 have been described with reference to FIG. 1 to FIG. 4. Because, in this example, the data acquisition device 150 is applied to the biosensor 100, the pair of terminals 153A of the ASIC 150A are connected to the pair of probes 140 via the wirings 131. The other configurations are the same as those shown in FIG. 1, and redundant explanation will be omitted here. If the data acquisition device 150 has the wireless communication unit 150TR, the wireless communication unit 150TR is connected to the memory 150C.

Figure 9:
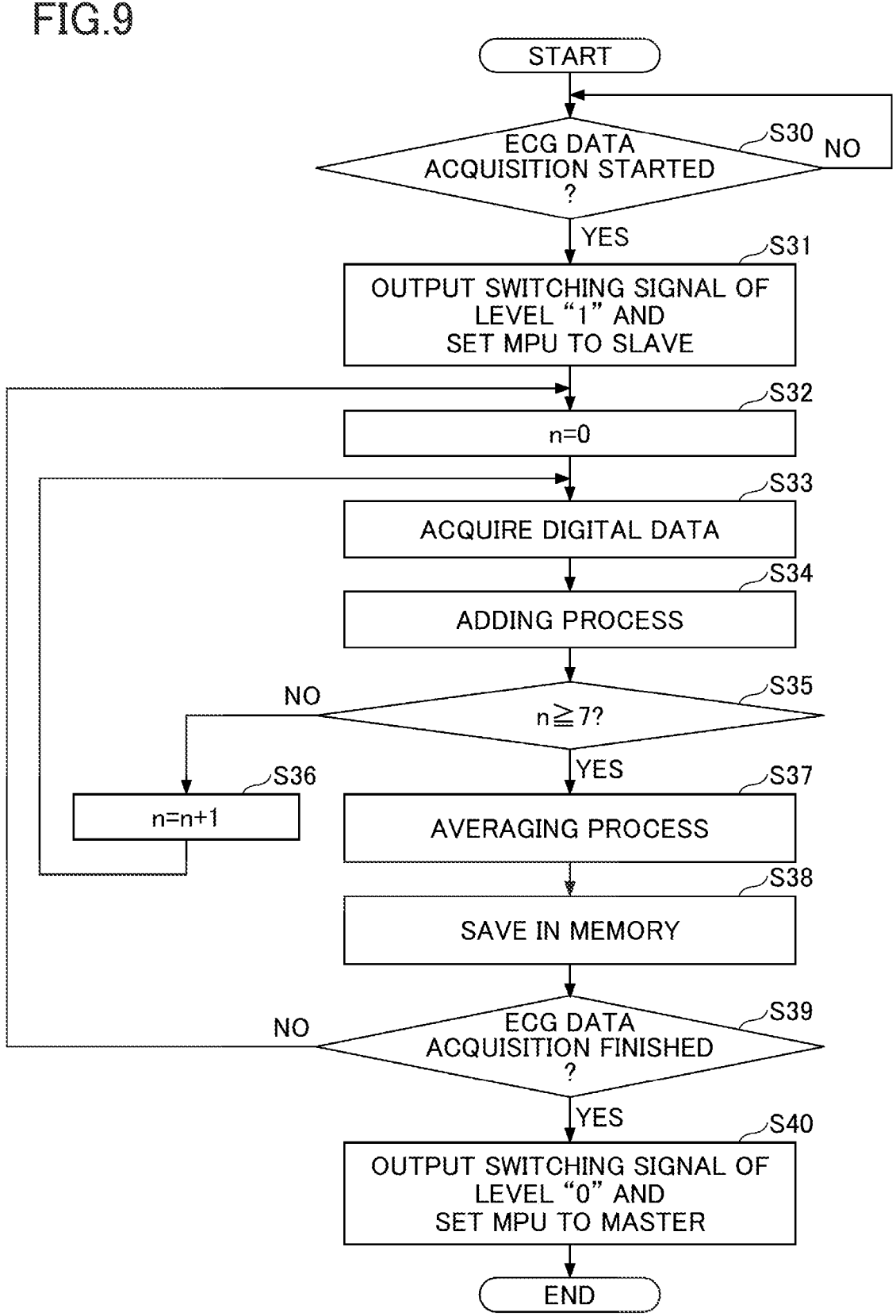
FIG. 9 is a flowchart showing a processing example of the MPU used in a biosensor.

FIG. 9 is a flowchart showing the operations of the MPU 150B when the data acquisition device 150 is applied to the biosensor 100. The operation flow of FIG. 9 shows a data processing process of the MPU 150B from the start to the end of acquisition and recording of electrocardiographic data, and is repeatedly executed over a predetermined period of time.

When the process starts, the MPU 150B determines whether acquisition of electrocardiographic data has started (step S30). This step may be implemented by determining whether analog electrocardiographic data have been input from the probes 140, whether a prescribed time has come, or the like. Step S30 is repeated until acquisition of electrocardiographic data has started (NO in S30). If the acquisition of electrocardiographic data has started (YES in S30), the switching setting part 152B sets the switching signal level to "1" and outputs the switching signal to the ASIC 150A, while setting the MPU 150B to the slave (step S31). The ASIC150A is set to the master by the level-1 switching signal. Upon being set to the master, the ADC 151A causes the ADC 151A to start analog to digital conversion.

The computing part 153B initializes the n value to zero (n=0) (step S32). The computing part 153B acquires digital electrocardiographic data from the ASIC 150A according to the CS signal (step S33). The computing part 153B performs addition according to the formula (2) (step S34).

$$A_{n+1} = A_n + x_n \quad (2)$$

The computing part 153B determines whether the n value is 7 or greater (step S35). If n is not equal to or greater than 7 (NO in S35), n is incremented (step S36). If it is determined by the computing part 153B in step S5 that n is 7 or greater (YES in S35), the computing part 153B calculates the average value (A8/8) using the sum A8 (step S37), and saves the average value (A8/8) in the memory 150C (step S38).

The main controller 151B determines whether the acquisition of electrocardiographic data is finished (step S39). This step may be implemented by determining whether the data transfer from the sensor 300 has not been carried out for a certain period of time or longer, whether prescribed time has elapsed from the start of acquisition of electrocardiographic data, whether the data occupancy of the memory 150C has exceeded a certain level, etc. The data acquisition device 150 may have a built-in timer. In this case, the main controller 151B may determine that the data acquisition has been completed when 24 hours have passed from the start of recording the digital electrocardiographic data.

If it is determined by the main controller 151B that the data acquisition has not been completed (NO in S39), the operation flow returns to step S32 to repeat steps S32 to S39. If it is determined by the main controller 151B that the data acquisition is finished (YES in S39), the switching setting part 152B sets the switching signal level to "0", and outputs the switching signal to the ASIC 150A, while setting the MPU 150B to the master (step S40). Upon being set to the slave by the switching signal of level "0", the ASIC 150A stops the ADC 151A from implementing the digital conversion process. Thus, the ASIC 150A causes the ADC 151A to perform digital conversion process during the period when the switching signal is at level "1", and causes the ADC 151A to terminate the digital conversion process when the switching signal transitions to level "0". In other words, the ADC 151A continues to perform the digital conversion process while the ASIC 150A is the master.

By the above-described process, the sum of multiple digital electrocardiographic data item is calculated, arithmetic averaging is performed, and data are saved in the memory 150C. This process is repeated over the period of the electrocardiographic data acquisition.

The biosensor 100 using the data acquisition device 150 acquires electrocardiographic data item xi ("i" is an integer of, for example, 0 to 7) in the corresponding time section Ti ("i" is an integer of 0 to 7) for acquiring electrocardiographic data, and carries out addition according to the formula (2) in the time section Tsb immediately after the electrocardiographic data acquisition section (see FIG. 3). In the time section TB immediately after the sum A8 of the electrocardiographic data items (x0 to x7) is obtained, only the average value (A8/8) is calculated using the sum A8. Thus, the biosensor 100 with reduced power consumption can be achieved.

The biosensor 100 configures the ASIC 150A to operate as the master, while setting the MPU 150B in the slave mode, during the period when the MPU 150B calculates the sums $A_{n+1}$ and the average value (A8/8) as shown in FIG. 3 (B). In this state, the frequency of the system clock of the MPU 150B is reduced to 4 MHz, which is equal to the sampling rate of the ADC 151A. This configuration also contributes to the reduction of power consumption.

The MPU 150B acquires digital electrocardiographic data from the ASIC 150A, while being set to the slave, when the CS signal transitions to the L level. The MPU 150B can acquire the digital electrocardiographic data without requesting the ASIC 150A to transmit the digital electrocardiographic data. The MPU 150B can immediately take in the digital electrocardiographic data acquired at the controller 270 from the ADC 151A. Thus, the biosensor 100 is capable of real-time operations.

Although the data acquisition device has been described based on example embodiments, the present invention is not limited to the above described embodiments. Various alterations or substitutions are available without deviating from the scope of the appended claims.

The present application is based upon and claims priority to earlier filed Japanese Patent Application Nos. 2019-060999 and 2019-061000, both filed Mar. 27, 2019. The entirety of both earlier-filed Japanese patent applications identified above is herein incorporated.

LISTING OF SYMBOLS 100 biosensor
140 probe
150 data acquisition device
150A ASIC
150B MPU
150C memory
150D, 150E bus
151A ADC
151B main controller
152B switching setting part 153B computing part
154B memory
160 buttery
300 sensor

What is claimed is:

1. A data acquisition device comprising:
an integrated circuit having a first terminal to which a master/slave switching signal is input at a start of data acquisition, an A/D converter for converting analog input data to digital data, and an output terminal for outputting the digital data, the integrated circuit operating in either a master mode or a slave mode according to the master/slave switching signal; and
an information processor having a switching setting part that generates the mater/slave switching signal, a second terminal connected to the first terminal and for outputting the master/slave switching signal, and an input terminal connected to the output terminal and for receiving the digital data, the switching setting part configuring the information processor to operate in the master mode when the integrated circuit operates in the slave mode, and to operate in the slave mode when the integrated circuit operates in the master mode,
wherein the integrated circuit is configured to output a synchronizing signal to the information processor to allow the information processor to acquire the digital data and configured to output the digital data from the output terminal when operating in the master mode according to the master/slave switching signal supplied from the information processor,
wherein the information processor is configured to generate a system clock and correct a timing of the system clock using the synchronizing signal supplied from the integrated circuit when the information processor is operating in the slave mode, and
wherein the information processor is configured to reduce a clock frequency when the information processor is operating in the slave mode compared to when the information processor is operating in the master mode.

2. The data acquisition device as claimed in claim 1, wherein the information processor generates a first switching signal as the master/slave switching signal for causing the integrated circuit to operate in the master mode at the start of data acquisition.

3. The data acquisition device as claimed in claim 1, wherein the information processor generates a second switching signal as the master/slave switching signal for switching between operations in the master mode and the slave mode at an end of data acquisition.

4. The data acquisition device as claimed in claim 1, wherein the information processor has a computing part that performs addition of the digital data item to calculate a sum every time the digital data item is acquired, until a predetermined number of digital data items are acquired, and that calculates an average value of the acquired digital items when the predetermined number of digital data items have been acquired.

5. The data acquisition device as claimed in claim 4, further comprising:
a memory connected to the information processor and configured to store the average value.

6. The data acquisition device as claimed in claim 1, wherein the integrated circuit is an application specific integrated circuit connected to the information processor by a serial peripheral interface (SPI) bus, and wherein the first terminal, the output terminal, the second terminal, and the input terminal are compatible with the SPI interface.

7. A biosensor comprising:
an electrode configured to be brought into contact with a subject;
a data acquisition device configured to acquire analog electrocardiographic data via the electrode; and
a wiring that connects the electrode and the data acquisition device,
wherein the data acquisition device includes an integrated circuit and an information processor,
wherein the integrated circuit has a first terminal to which a master/slave switching signal is input at a start of acquisition of the analog electrocardiogram the subject, an A/D converter for converting the analog electrocardiographic data to digital electrographic data, and an output terminal for outputting the digital electrocardiographic data, the integrated circuit operating in either a master mode or a slave mode according to the mater/slave switching signal,
wherein the information processor has a switching setting part that generates the master/slave switching signal, a second terminal connected to the first terminal and configured to output the master/slave switching signal, and an input terminal connected to the output terminal and configured to receive the digital electrocardiographic data, the switching setting part configuring the information processor to operate in the master mode when the integrated circuit operates in the slave mode, and to operate in the slave mode when the integrated circuit operates in the master mode, and
wherein the integrated circuit outputs a synchronizing signal to the information processor to allow the information processor to acquire the digital electrocardiographic data and outputs the digital electrocardiogram the output terminal when the integrated circuit operates in the master according to the master/slave switching signal supplied from the information processor,
wherein the information processor generates a system clock and corrects a timing of the system clock using the synchronizing signal supplied from the integrated circuit when the information processor is operating in the slave mode, and
wherein the information processor reduces a clock frequency when the information processor is operating in the slave mode compared to when the information processor is operating in the master mode.

8. The biosensor as claimed in claim 7, wherein the information processor generates a first switching signal as the master/slave switching signal for configuring the integrated circuit to operate in the master mode at the start of acquisition of the electrocardiographic data.

9. The biosensor as claimed in claim 7, wherein the information processor generates a second switching signal as the master/slave switching signal for switching between operations in the master mode and the slave mode at an end of acquisition of the electrocardiographic data from the subject.

10. The biosensor as claimed in claim 9, wherein the information processor terminates acquisition of the electrocardiographic data when 24 hours has elapsed from the start of acquisition of the electrocardiographic data.

11. The biosensor as claimed in claim 7, wherein the information processor has a computing part that performs addition of the digital electrocardiogram to calculate a sum every time the digital electrocardiographic data item is acquired, until a predetermined number of digital electrocardiograms are acquired, and that calculates an average value of the acquired digital electrocardiographic data items when the predetermined number of digital electrocardiographic data items have been acquired.

12. The biosensor as claimed in claim 7, further comprising:
- a pressure-sensitive adhesive layer configured to adhere to the subject; and
- a base material layer provided on a surface opposite to the adhering surface of the pressure-sensitive adhesive layer,
- wherein the electrode is fixed to the pressure-sensitive adhesive layer, and the data acquisition device is provided on the base material layer.

* * * * *